US009157788B2

(12) United States Patent
Hunter et al.

(10) Patent No.: US 9,157,788 B2
(45) Date of Patent: Oct. 13, 2015

(54) PART EVALUATION SYSTEM/METHOD USING BOTH RESONANCE AND SURFACE VIBRATION DATA

(75) Inventors: Lemna J. Hunter, Corrales, NM (US); Leanne Jauriqui, Albuquerque, NM (US); Greg Weaver, Rio Rancho, NM (US)

(73) Assignee: VIBRANT CORPORATION, Albuquerque, NM (US)

( * ) Notice: Subject to any disclaimer, the term of this patent is extended or adjusted under 35 U.S.C. 154(b) by 286 days.

(21) Appl. No.: 13/526,996

(22) Filed: Jun. 19, 2012

(65) Prior Publication Data

US 2013/0074600 A1 Mar. 28, 2013

Related U.S. Application Data

(60) Provisional application No. 61/498,656, filed on Jun. 20, 2011.

(51) Int. Cl.
*G01H 13/00* (2006.01)
*G01N 29/12* (2006.01)
*G01N 29/22* (2006.01)
*G01N 29/44* (2006.01)

(52) U.S. Cl.
CPC ............. *G01H 13/00* (2013.01); *G01N 29/12* (2013.01); *G01N 29/223* (2013.01); *G01N 29/44* (2013.01); *G01N 2291/014* (2013.01); *G01N 2291/017* (2013.01); *G01N 2291/103* (2013.01)

(58) Field of Classification Search
CPC ......... G01H 9/00; G01H 9/002; G01H 9/008; G01H 13/00; G01H 7/00; G01N 29/045; G01N 1/06; G01N 1/16; G01N 7/00; G01N 29/24; G01N 29/06; G01N 29/04; G01N 29/12; G01N 29/348; G01N 29/42; G01N 29/46; G01N 2291/014; G01N 2291/0423; G01N 29/2418; G01N 2291/103; G01N 2291/017; G01N 2291/01
USPC ............ 73/579, 602, 643, 587, 623, 648, 659
See application file for complete search history.

(56) References Cited

U.S. PATENT DOCUMENTS

| 4,858,469 A * | 8/1989 | Hosgood et al. ................ 73/579 |
| 5,408,880 A * | 4/1995 | Rhodes et al. .................. 73/579 |
| 5,425,272 A * | 6/1995 | Rhodes et al. .................. 73/579 |
| 5,495,763 A * | 3/1996 | Rhodes et al. .................. 73/579 |
| 5,631,423 A * | 5/1997 | Rhodes .......................... 73/579 |
| 5,641,905 A * | 6/1997 | Schwarz et al. ................ 73/579 |
| 5,837,896 A | 11/1998 | Rhodes et al. |

(Continued)

OTHER PUBLICATIONS

Hirao M., et al., "Interface Delamination of Layered Media: Acoustic Spectroscopy and Modal Analysis", IEEE Transactions on Ultrasonics, Ferroelectrics and Frequency Control, IEEE, US, vol. 51, No. 4, pp. 439-443, Apr. 1, 2004.

(Continued)

*Primary Examiner* — Laura Martin
*Assistant Examiner* — Rose M Miller
(74) *Attorney, Agent, or Firm* — Marsh Fischmann & Breyfogle LLP

(57) ABSTRACT

A part (120) may be subjected to both a resonance inspection and a surface vibration inspection. Various protocols (230; 240; 250; 280; 260) are disclosed as to how the results of one or more of these inspections may be used to evaluate the part (120).

30 Claims, 27 Drawing Sheets

(56) References Cited

U.S. PATENT DOCUMENTS

| | | | |
|---|---|---|---|
| 5,886,263 A | 3/1999 | Nath et al. | |
| 5,952,576 A | 9/1999 | Schwarz | |
| 5,965,817 A * | 10/1999 | Schwarz et al. | 73/579 |
| 5,992,234 A | 11/1999 | Rhodes et al. | |
| 6,199,431 B1 * | 3/2001 | Nath et al. | 73/579 |
| 7,089,796 B2 * | 8/2006 | Pepper et al. | 73/602 |
| 2008/0257047 A1 | 10/2008 | Pelecanos et al. | |
| 2009/0079424 A1 | 3/2009 | Tralshawala et al. | |
| 2010/0191107 A1 | 7/2010 | Bowers et al. | |

OTHER PUBLICATIONS

Amziane, A., et al., "Laser Ultrasonics Evaluation and Testing of Coated HTR Nuclear Fuel", Proceedings of SPIE, 808224, pp. 1-10, May 23, 2011.

Jauriqui, L., et al., "A More Comprehensive NDE: PCRT for Ceramic Components", Review of Progress in Quantitative Nondestructive Evaluation, vol. 30, pp. 997-1004, AIP Conf. Proc. 1335, 2011.

\* cited by examiner

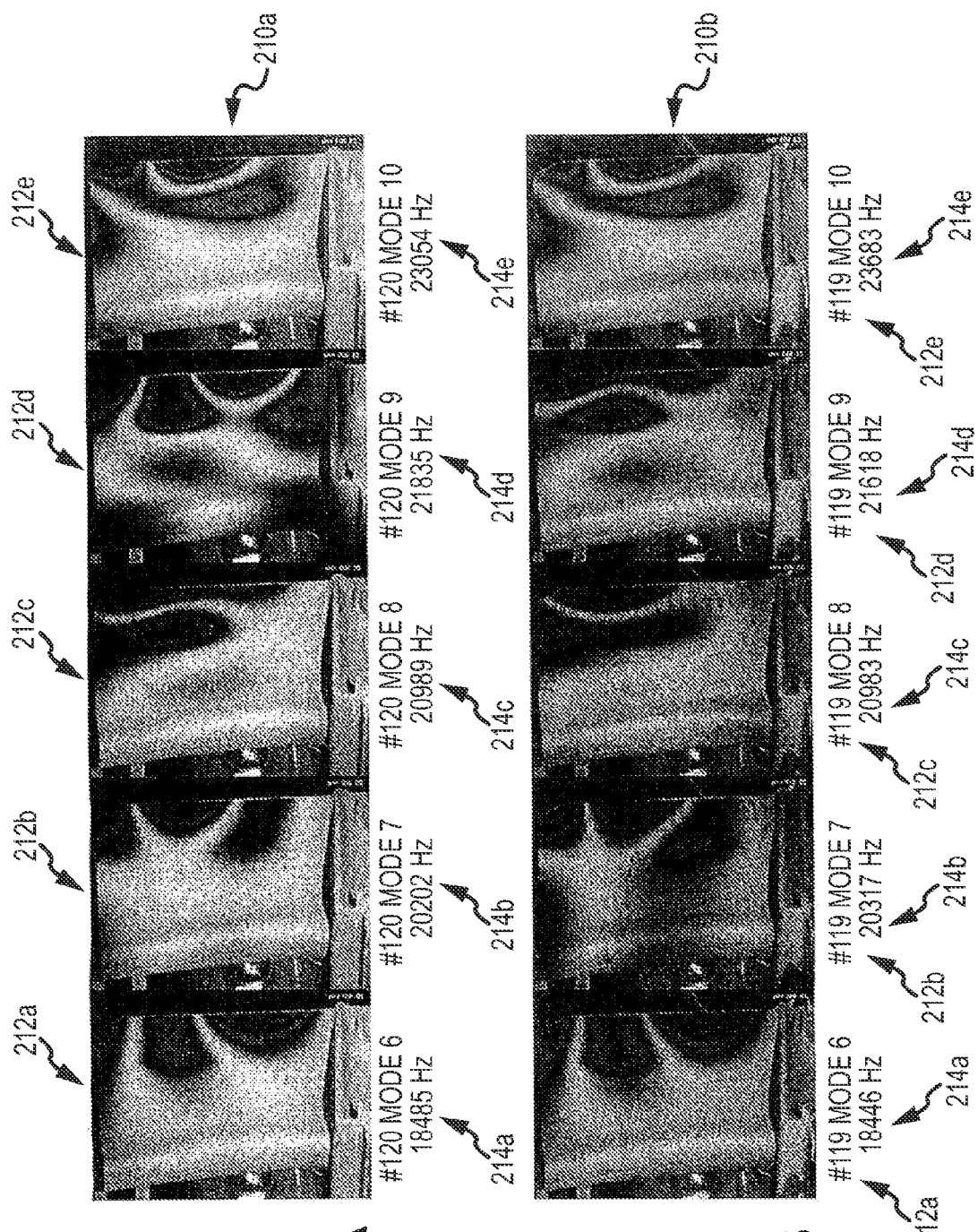

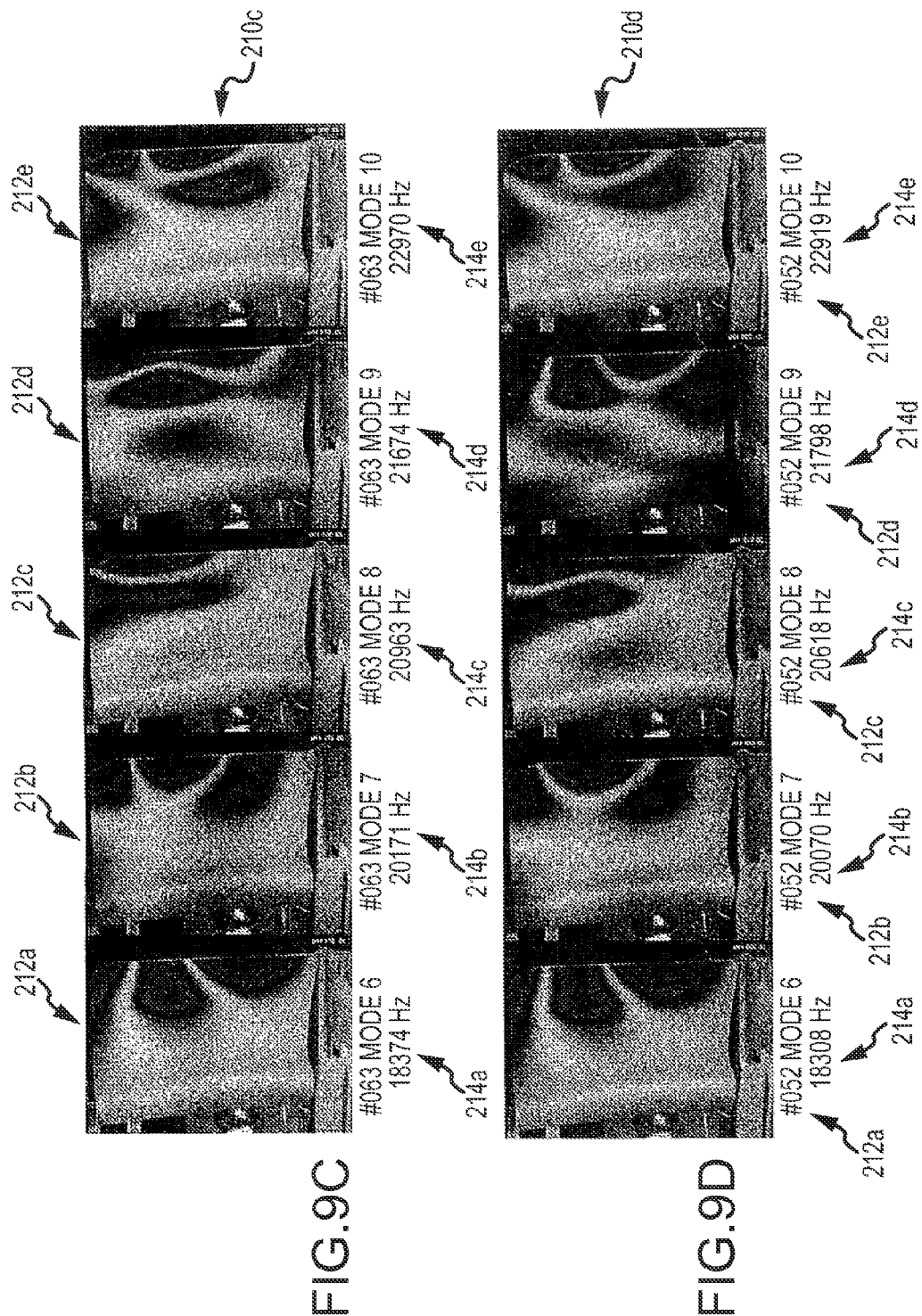

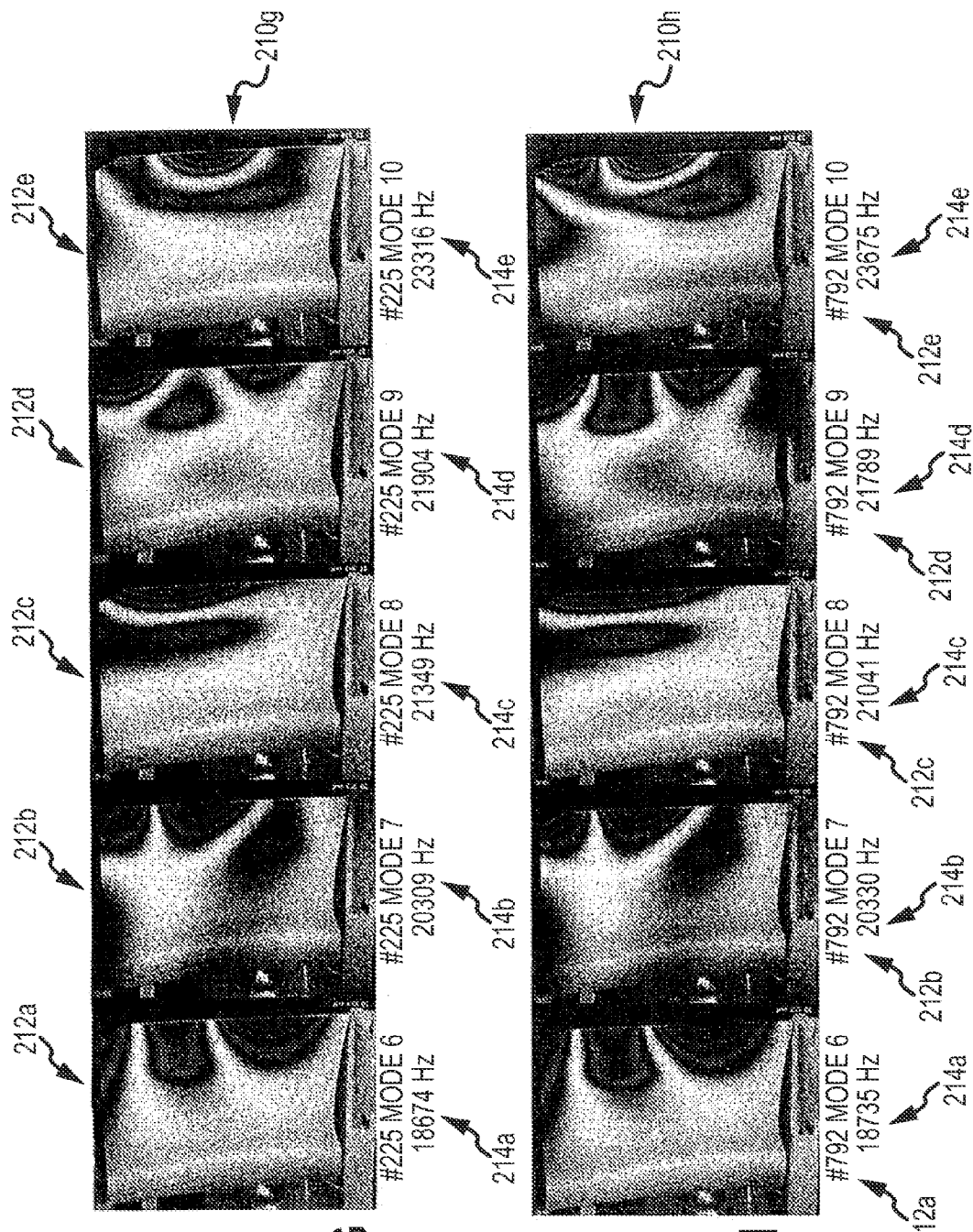

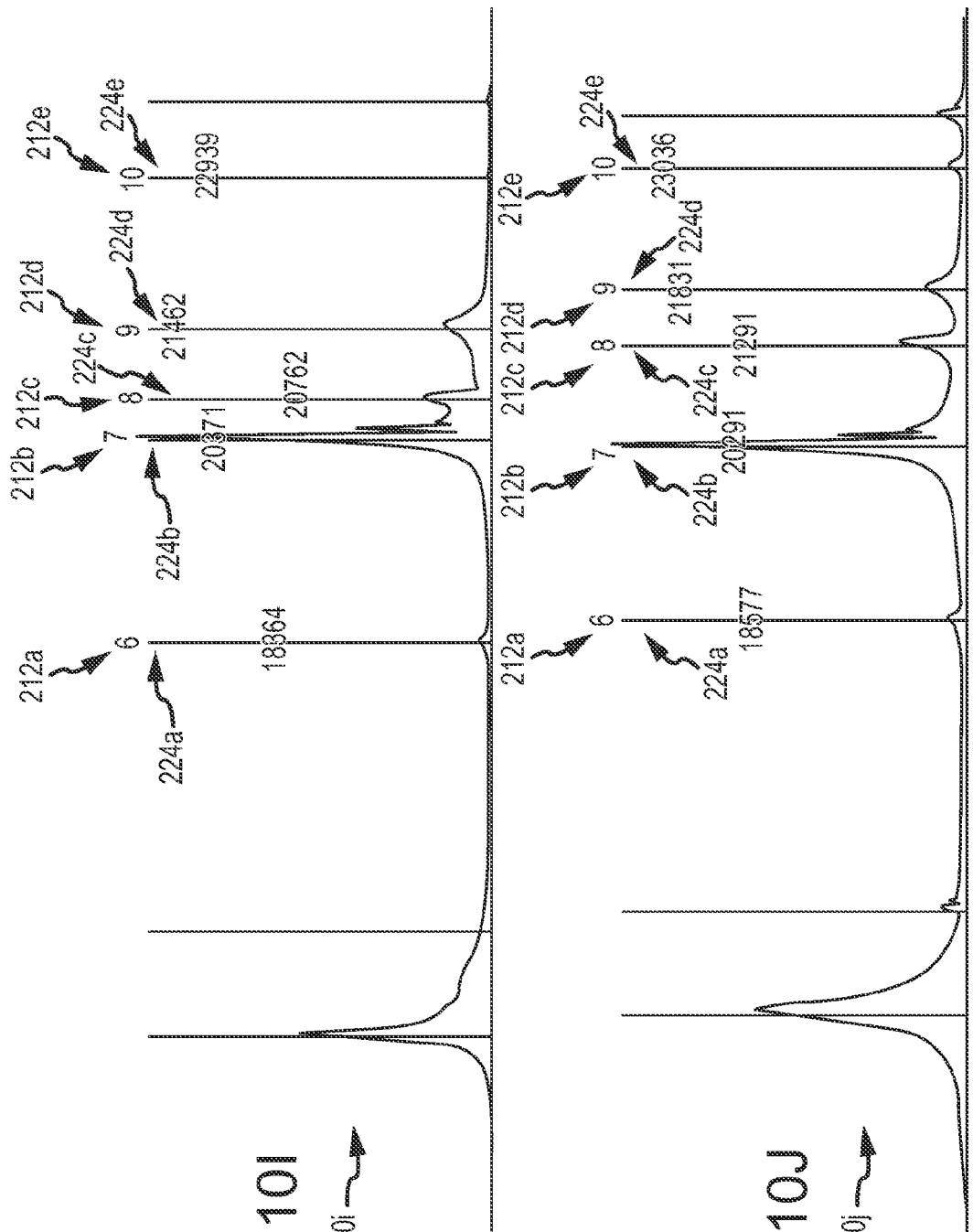

PART EVALUATION SYSTEM/METHOD USING BOTH RESONANCE AND SURFACE VIBRATION DATA

CROSS-REFERENCE TO RELATED APPLICATIONS

This patent application is a conversion of, and claims priority to, U.S. Provisional Patent Application Ser. No. 61/498,656, entitled "PART EVALUATION SYSTEM/METHOD USING BOTH RESONANCE AND SURFACE VIBRATION DATA," filed on Jun. 20, 2011, and the entire disclosure of which is hereby incorporated by reference in its entirety herein.

FIELD OF THE INVENTION

The present invention generally relates to the field of testing parts and, more particularly, to the field of resonance inspection of parts that involves exciting a part at a number of different frequencies and obtaining the frequency response of the part to the various excitations.

BACKGROUND

A variety of techniques have been developed in which parts may be tested "nondestructively," meaning that the testing methodology enables defects to be identified without causing damage to the part. Examples of such nondestructive-testing methodologies include acoustic techniques, magnetic-particle techniques, liquid-penetrant techniques, radiographic techniques, eddy-current testing, and low-coherence interferometry, among others. There are various known advantages and disadvantages to each of these categories of testing methodologies, which are accordingly used in different environments.

Nondestructive-testing methods that use acoustic radiation generally operate in the ultrasonic range of the acoustic spectrum, and are valuable for a number of reasons. Such techniques are sensitive, for example, to both surface and subsurface discontinuities, enabling identification of defects both within the bulk and near the surface of a part. The depth of penetration for defect detection is generally superior to many other nondestructive-testing methodologies, and the techniques are highly accurate not only in determining the position of a defect, but also in estimating its size and shape.

SUMMARY

The present invention is embodied by a method of evaluating a part, where two different types of inspections may be conducted—a resonance inspection and a surface vibration inspection. A resonance inspection includes exciting a given part at a plurality of input frequencies and obtaining a frequency response of the part (e.g., to acquire/assess resonance data). A surface vibration inspection includes vibrating a given part and assessing surface vibrations of this part (e.g., to acquire/assess surface vibration data).

A first inspection is conducted on a first part-under-test, where this first inspection is in the form of a resonance inspection. A second inspection is conducted on the first part-under-test, where this second inspection is in the form of a surface vibration inspection. The first part-under-test may be evaluated based in at least some manner upon the first and second inspections.

A number of feature refinements and additional features are applicable to the present invention. These feature refinements and additional features may be used individually or in any combination. Original equipment manufacturer or OEM parts may be evaluated using the present invention. Non-OEM parts may also be evaluated using the present invention, for instance for purposes of determining whether a non-OEM part complies with an OEM part or other control group (of one or more other parts and/or part specifications).

The first part-under-test may be in the form of an in-service part. An in-service part may be characterized as a part that has been released from production for use in one or more end-use applications. An "in-service part" in the context of the present invention encompasses a part that has been used to at least some extent after having been released by the manufacturer. An in-service part may be a part that has been put into use by a party other than the manufacturer (e.g., a customer or end user). Although an in-service part could be used autonomously or independently of any other parts, an in-service part may be incorporated by an appropriate assembly or system (e.g., a turbine blade (an in-service part) in a jet engine (an assembly or system)).

The present invention may also be used to evaluate new production parts (e.g., the first part-under-test may be a new production part). A new production part may be characterized as a newly manufactured part that has not yet been released from production (e.g., parts that have not yet been shipped for use by an end user or customer). New production parts include parts that may have undergone at least some post-production testing of any appropriate type (including without limitation a resonance inspection and a surface vibration inspection in accordance with the present invention).

A resonance inspection may be characterized as obtaining a whole body frequency response of the first part-under-test using a number of different drive or input frequencies. A resonance inspection of the first part-under-test may utilize a first transducer that excites or drives the first part-under-test at multiple frequencies (e.g., by sweeping through a predetermined range of frequencies in any appropriate manner), along with at least one other transducer that measures the frequency response of this first part-under-test to such excitations or drive frequencies (e.g., thereby encompassing using two "receiver" transducers). Any number of frequencies may be used to excite the first part-under-test for the resonance inspection, and the excitation frequencies may be input to the first part-under-test in any appropriate pattern and for any appropriate duration. Another option is to use a single transducer for performing a resonance inspection of the first part-under-test. In this case, a transducer may drive the first part-under-test at a certain frequency for a certain amount of time, and thereafter this same transducer may be used to obtain the frequency response of the first part-under-test (e.g., after terminating the driving of the transducer at an input frequency). This may be repeated for multiple input or drive frequencies.

A frequency response may be in the form of a plot of a collection of responses of the part-under-test at each frequency that may be used to drive the part-under-test. For instance, if the part-under-test is driven at frequency the amplitude of the response of the part-under-test at this same frequency $f_1$ may be included in the noted plot at the frequency $f_1$; if the part-under-test is driven at frequency $f_2$, the amplitude of the response of the part-under-test at this same frequency $f_2$ may be included in the plot at the frequency $f_2$; if the part-under-test is driven at frequency $f_3$, the amplitude of the response of the part-under-test at this same frequency $f_3$ may be included in the plot at this frequency $f_3$; and so forth. Any such plot is within the scope of a "frequency response" as set forth herein.

Any appropriate combination of excitation or drive frequencies may be used for a resonance inspection for purposes of the present invention. Each transducer that is used to perform a resonance inspection for purposes of the present invention may be of any appropriate size, shape, configuration, and/or type. Although a resonance inspection for purposes of the present invention could be performed in situ (e.g., with the part in an installed condition or state, for instance on a turbine blade that is mounted within a jet engine), such a resonance inspection could be performed on a part that has been removed from service (e.g., at a time when the part is in an uninstalled condition or state, for instance on a turbine blade that has been removed from a jet engine and positioned within an appropriate fixture).

The resonance inspection of the first part-under-test may include using at least one transducer that excites the first part-under-test through a range of frequencies, and using at least two other transducers to measure the frequency response of the first part-under-test. Another option for the resonance inspection of the first part-under-test is to use a first transducer that excites the first part-under-test at a number of different frequencies, and using this same first transducer to measure the frequency response of the first part-under-test.

A resonance inspection for purposes of the present invention may include exciting the first part-under-test using at least one drive transducer that is in contact with the first part-under-test. Another option for a resonance inspection in the present invention is to excite the first part-under-test using at least one drive transducer that is maintained in spaced relation to the first part-under-test throughout the resonance inspection. In one embodiment, such a drive transducer (e.g., a drive transducer that is spaced from the first part-under-test for the resonance inspection) may be in the form of a laser. Representative lasers that may be used as a drive transducer for conducting a resonance inspection on the first part-under-test include without limitation Nd:YAG lasers, TEA $CO_2$ lasers, excimer lasers, or diode lasers.

A resonance inspection of the first part-under-test may entail obtaining a frequency response of this part using at least one receive transducer that is in contact with the first part-under-test. Another option for the resonance inspection is to obtain a frequency response of the first part-under-test using at least one receive transducer that is maintained in spaced relation to this first part-under-test. In one embodiment, a receive transducer used in the resonance inspection of the first part-under-test is in the form of a laser. Representative lasers that may be used as a receive transducer for conducting a resonance inspection on the first part-under-test include without limitation helium-neon lasers, laser diodes, fiber lasers, and ND:YAG lasers. The resonance inspection of the first part-under-test may include obtaining a frequency response of this first part-under-test using laser vibrometry. The frequency response of the first part-under-test in this case may be obtained from a single location using laser vibrometry. Another option for this case is to obtain the frequency response of the first part-under-test by laser scanning multiple locations on the surface of this first part-under-test.

The frequency response from the resonance inspection of the first part-under-test may be compared with a resonance standard of any appropriate type. Such a resonance standard may be stored on a computer-readable storage medium. For instance, the resonance standard may be stored on a hard drive, disk drive, optical drive, flash drive, or the like, that is utilized by a computer for making the comparison in accordance with the present invention. In any case, the comparison of the frequency response from the resonance inspection of the first part-under-test with the resonance standard may utilize at least one processor (e.g., one or more processors of any appropriate type, where multiple processors may be integrated/implemented to define any appropriate processing architecture). In one embodiment, the resonance standard is equated with at least certain resonance attributes of a new production part. In another embodiment, the resonance standard is equated with at least certain resonance attributes of a normally aging of a part.

The resonance standard, against which the frequency response from the resonance inspection of the first part-under-test may be compared, may be of any appropriate type and/or defined in any appropriate manner. One embodiment has this resonance standard including spectra (e.g., a "snapshot" of the whole body frequency response of a part at one or more points in time) of at least one other part. Another embodiment has this resonance standard being in the form of a mathematical model (e.g., resonance inspection results generated from software based upon projections/predictions).

The resonance standard which may be used by the present invention may be based upon resonance inspection data from a single part or a population of parts. In one embodiment, the population of parts does not include the first part-under-test. In any case, the resonance standard may be in the form of one or more representative spectra (e.g., one spectra for each of a plurality of parts that are part of the noted population). A given representative spectra may also be in the form of an average of spectra from each of the plurality of parts that are included within the noted population. The resonance standard may also be in the form of spectra from a single member of the population.

The surface vibration inspection used by the present invention may be of any appropriate type and may be executed in any appropriate manner. Representative surface vibration for purposes of the present invention include without limitation holographic interferometry, laser vibrometry, laser Doppler velocimetry, scanning laser vibrometry, and 2-d and 3-d scanning laser vibrometry.

The evaluation of the first part-under-test in the case of the present invention may include determining if the first part-under-test is equivalent to a control group. For instance, the present invention may be used to determine if non-OEM parts should be accepted. "Acceptance" may be equated with a non-OEM part being determined by the present invention to be equivalent to a corresponding OEM part (such that the non-OEM part may be used in place of the OEM part).

The resonance inspection and the surface vibration inspection of the first part-under-test may be conducted while the first part-under-test is retained within an appropriate fixture. For instance, the first part-under-test may be disposed within a fixture, and each of the resonance inspection and the surface vibration inspection may be conducted on the first part while being retained by this fixture (and without having to remove the first part-under-test from the fixture until each of the resonance inspection and the surface vibration inspection have been completed (at least the data acquisition portions of each such inspection).

The resonance inspection and the surface vibration inspection of the first part-under-test may be simultaneously executed (e.g., at least the data acquisition portion for each of these inspections). Another option is for the resonance inspection and the surface vibration inspection of the first part-under-test to be undertaken at different times (e.g., at least the data acquisition portion for each of these inspections). For instance, the resonance inspection could be conducted on the first part-under-test (e.g. at least the acquisition of data from this resonance inspection), followed by the surface vibration inspection (e.g. at least the acquisition of data from this surface vibration inspection). Alternatively, the surface vibration inspection could be conducted on the first part-under-test (e.g. at least the acquisition of data from this surface vibration inspection), followed by the resonance inspection (e.g. at least the acquisition of data from this resonance inspection). It should be appreciated that the analysis of the results provided by each of the resonance and surface vibration inspections may be undertaken at any appropriate time and in any appropriate manner.

The evaluation of the first part-under-test in the case of the present invention may entail using the results from the resonance inspection of the first part-under-test to assess at least one anomaly in the results from the surface vibration inspection of this first part-under-test. The evaluation of the first part-under-test in the case of the present invention may also entail using the results from the surface vibration inspection of the first part-under-test to assess at least one anomaly in the results from the resonance inspection of this first part-under-test.

The evaluation of the first part-under-test for the present invention may entail using results from the surface vibration inspection to associate a first resonance frequency peak (such a frequency peak being in results from the resonance inspection of the first part-under-test) with a particular vibrational mode or mode shape. The evaluation of the first part-under-test for the present invention may entail using results from the surface vibration inspection to associate each of a plurality of resonance frequency peaks (such frequency peaks being in results from the resonance inspection of the first part-under-test) with a particular vibrational mode or mode shape. The evaluation of the first part-under-test for the present invention may also be characterized as using results from the surface vibration inspection of the first part-under-test to identify at least one vibrational mode or mode shape in results from the resonance inspection of this first part-under-test. Representative vibrational modes or mode shapes in accordance with the foregoing include without limitation a bending mode, a torsional mode, longitudinal modes, coupling modes, flexural modes, and axial modes.

A plurality of vibrational modes or mode shapes may be identified in results from the surface vibration inspection of the first part-under-test. These vibrational modes or mode shapes may be identified in any appropriate manner, for instance utilizing modeling, mathematical derivation, or any combination thereof. In any case, the identification of vibrational modes or mode shapes may be utilized in the resonance inspection of the first part-under-test. For instance, the vibrational modes or mode shapes identified in results from the surface vibration inspection of the first part-under-test may be used in the assessment of results provided by the resonance inspection of the first part-under-test. In one embodiment, the identification of the vibrational modes or mode shapes in results from the surface vibration inspection of the first part-under-test is used to identify an associated frequency, and these frequencies may be used in the assessment of results of the resonance inspection of the first part-under-test. The frequencies associated with the vibrational or modes shapes in the surface vibration inspection results may be used to assign resonance frequency peaks in the resonance inspections results to the proper vibrational mode or mode shape.

At least one resonance standard may be used in conducting a resonance inspection of the first part-under-test and as previously noted. Any resonance inspection-based comparison between the first part-under-test and such a resonance standard may be directed to determining if the first part-under-test is at least functionally equivalent with a part(s) used to define the noted resonance standard. "Functionally equivalent" includes where the parts are manufactured from common design specifications. However, "functionally equivalent" also encompasses the situation where parts are manufactured from different design specifications, but which may be used in the same end-use application. For instance, a given engine may allow turbine blades to be manufactured from either of a pair of design specifications. Resonance inspection-based comparisons for purposes of the present invention may be made between turbine blades used by the noted engine, but which are manufactured from the noted different design specifications. Typically, the differences between parts that are subject to a resonance inspection-based comparison for purposes of the present invention will not be of a radical nature (e.g., the parts will be on the same class (e.g., turbine blades); the parts will be very similar dimensionally).

The evaluation of the first part-under-test may be characterized as using the results from the surface vibration inspection of the first part-under-test in the comparison of results from the resonance inspection of the first part-under-test with a resonance standard. For instance, results from the surface vibration inspection of the first part-under-test may be used to associate one or more resonance frequency peaks in results from the resonance inspection of the first part-under-test with a vibrational mode or mode shape, and then one or more of these associated resonance frequency peaks may be compared to an appropriate resonance standard.

A resonance standard that is used in conducting a resonance inspection of the first part under-test may reflect results from one or more surface vibration inspections. Consider the case where a separate resonance inspection is conducted on each of a plurality of parts (e.g., a population of parts), and where a separate surface vibration inspection is also conducted on each of these same parts (e.g., on each of the parts that define the population). Results of the surface vibration inspection conducted on one part may be correlated with results of the resonance inspection conducted on this same part (e.g., such that the resonance data is collimated according to mode shape). This may be done for each of a plurality of parts (e.g., the parts within the population), and a resonance standard may use the correlated results from the resonance and surface vibration inspections of a least one part (including from a plurality of parts in the population).

A resonance standard that is used in conducting a resonance inspection of the first part under-test may reflect results from a thermal analysis. Consider the case where a separate resonance inspection is conducted on each of a plurality of parts (e.g., a population of parts), and where a separate thermal surface analysis is also conducted on each of these same parts (e.g., on each of the parts that define the population). Results of the surface vibration inspection conducted on one part may be correlated with results of the thermal surface analysis conducted on this same part (e.g., such that the resonance data is collimated according to mode shape). This may be done for each of a plurality of parts (e.g., the parts within the population), and a resonance standard may use the correlated results from the resonance inspection and thermal surface analysis of a least one part (including from a plurality of parts in the population).

The present invention may be used in a number of implementations. The present invention may be used to assess whether parts from one manufacturer (e.g., non-OEM) are sufficiently similar to, equivalent to, etc., parts from another manufacturer (e.g., an OEM). For instance, the first part-under-test may be characterized as being a member of a first part group that includes a plurality of parts, and the present invention may be used to compare the first part group with the second part group (where the second part group also includes a plurality of parts).

The present invention may be used to assess the manufacturing operations of a particular manufacturer. Consider the case where the method of the present invention is executed on each of a first plurality of parts that were manufactured over a first time frame, where each part in this first plurality of parts was to be manufactured in accordance with first specifications. The method of the present invention may also be executed on each of a second plurality of parts that were manufactured over a second time frame (different from the first time frame), where each part in this second plurality of parts was also to be manufactured in accordance with first specifications. The first and second plurality of parts may have been manufactured by a common manufacturer, and may in fact have been manufactured by common machine/system (e.g., a "manufacturing setup"). The present invention may be utilized to assess the manufacturing operations of this common manufacturer based upon differences in results provided by the method.

The first-part-under-test may include a plurality of common first structures (e.g., a plurality of fins of common dimensions). The evaluation in accordance with the present invention may include conducting a separate resonance inspection on each of these first structures when results from the resonance inspection of the first part-under-test include at least one anomaly, when results from the surface vibration inspection of the first part-under-test include at least one anomaly, or both. That is, the method may entail conducting a single resonance inspection and a single surface vibration inspection of the first part-under-test, unless an anomaly is identified in results from one or more of these inspections. Upon identifying such an anomaly, a separate resonance inspection may thereafter be conducted on each of a plurality of first structures (e.g., to attempt to identify which particular first structure potentially includes one or more defects).

The present invention may be configured to undertake the surface vibration inspection of the first part-under-test only if there is at least one anomaly in results provided by the resonance inspection of this first part-under-test. Another option is for the present invention to be configured to undertake the resonance inspection of the first part-under-test only if there is at least one anomaly in results provided by the surface vibration inspection of this first part-under-test. Yet another option is for the present invention to be configured to conduct both a resonance inspection and a surface vibration inspection in each instance where a part is evaluated by the present invention.

The evaluation of the first part-under-test may include identifying a phase shift using the resonance inspection of the first part-under-test (e.g., by reviewing results of the first resonance inspection and identifying a phase shift, for instance a phase shift between a drive signal and a response signal), and thereafter using the surface vibration inspection of this first part-under-test to attempt to identify a possible cause of this phase shift. In one embodiment, the evaluation of the first part-under-test includes identifying an existence of a defect in the first part-under-test by identifying a phase shift from the resonance inspection, and thereafter identifying a location of this defect from results of the surface vibration inspection. Representative surface inspection interpretation methods in accordance with the foregoing include without limitation Modal Assurance Criteria (MAC) methods, specific localized modal pattern variations and minute modal contrast variations. For instance, results of the resonance inspection of the first part-under-test may include a phase shift, and which may be equated with the existence of a defect, and results of the surface vibration inspection may identify the location that produced this phase shift (and thereby the location of the defect).

The evaluation of the first part-under-test may include identifying a change in amplitude using the first resonance inspection of the first part-under-test (e.g., by reviewing results of the first resonance inspection and identifying a change in amplitude, for instance a change in amplitude between a drive signal and a response signal), and thereafter using the surface vibration inspection of this first part-under-test to attempt to identify a possible cause of this change in amplitude. In one embodiment, the evaluation of the first part-under-test includes identifying an existence of a defect in the first part-under-test by identifying a change in amplitude from the resonance inspection, and thereafter identifying a location of this defect from results of the surface vibration inspection. Representative surface inspection interpretation methods in accordance with the foregoing include without limitation Modal Assurance Criteria (MAC) methods, specific localized modal pattern variations and minute modal contrast variations. For instance, results of the resonance inspection of the first part-under-test may include a change in amplitude, and which may be equated with the existence of a defect, and results of the surface vibration inspection may identify the location that produced this change in amplitude (and thereby the location of the defect).

The present invention may further include modeling a defect in a particular part. The evaluation of the first part-under-test may include comparing results from the resonance inspection of the first part-under test with the noted model, may include comparing results from the surface vibration inspection of the first part-under test with the noted model, or both.

Any feature of the present invention that is intended to be limited to a "singular" context or the like will be clearly set forth herein by terms such as "only," "single," "limited to," or the like. Merely introducing a feature in accordance with commonly accepted antecedent basis practice does not limit the corresponding feature to the singular (e.g., indicating that a resonance inspection system utilizes "a frequency response transducer" alone does not mean that the resonance inspection system utilizes only a single frequency response transducer). Moreover, any failure to use phrases such as "at least one" also does not limit the corresponding feature to the singular (e.g., indicating that a resonance inspection system utilizes "a frequency response transducer" alone does not mean that the resonance inspection system utilizes only a single frequency response transducer). Use of the phrase "at least generally" or the like in relation to a particular feature encompasses the corresponding characteristic and insubstantial variations thereof (e.g., indicating that a structure is at least generally cylindrical encompasses the structure being cylindrical). Finally, a reference of a feature in conjunction with the phrase "in one embodiment" does not limit the use of the feature to a single embodiment.

BRIEF DESCRIPTION OF THE FIGURES

FIGS. 9A-J each present surface vibration data (for a particular drive frequency) for a part that has undergone a surface vibration inspection.

FIGS. 10A-J each present resonance data (for the corresponding drive frequencies of FIGS. 9A-J) for a part that has undergone a resonance inspection.

DETAILED DESCRIPTION

Various applications of resonance inspection (e.g., resonance ultrasound spectroscopy; process compensated resonance testing) are addressed herein. Various principles that may relate to resonance inspection are addressed in the following U.S. patents, the entire disclosures of which are incorporated by reference in their entirety herein: U.S. Pat. Nos. 5,408,880; 5,425,272; 5,495,763; 5,631,423; 5,641,905; 5,837,896; 5,866,263; 5,952,576; 5,965,817; 5,992,234; and 6,199,431.

Figure 1:
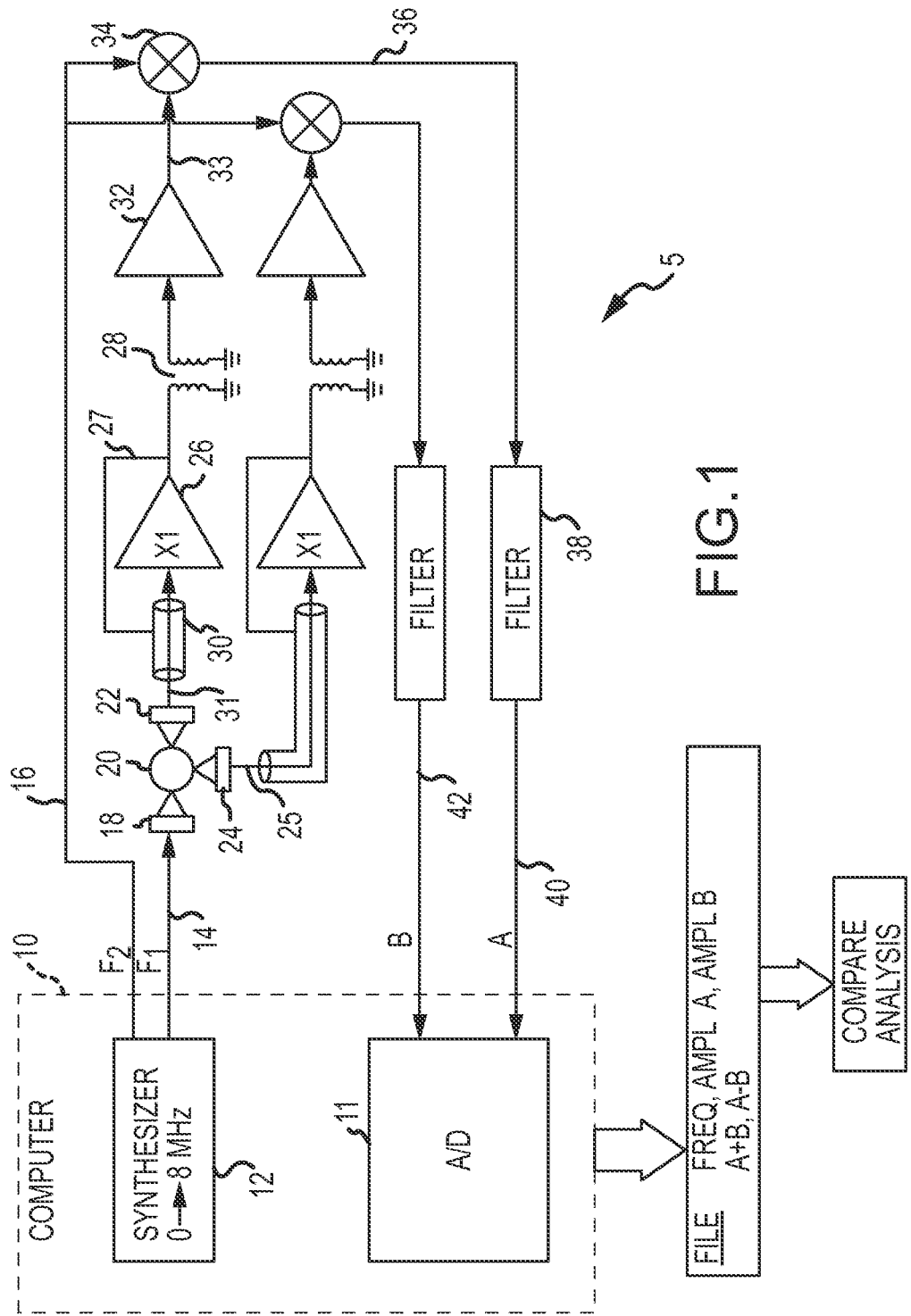
FIG. 1 is a block-diagram of one embodiment of a resonance inspection tool.
Figure 2:
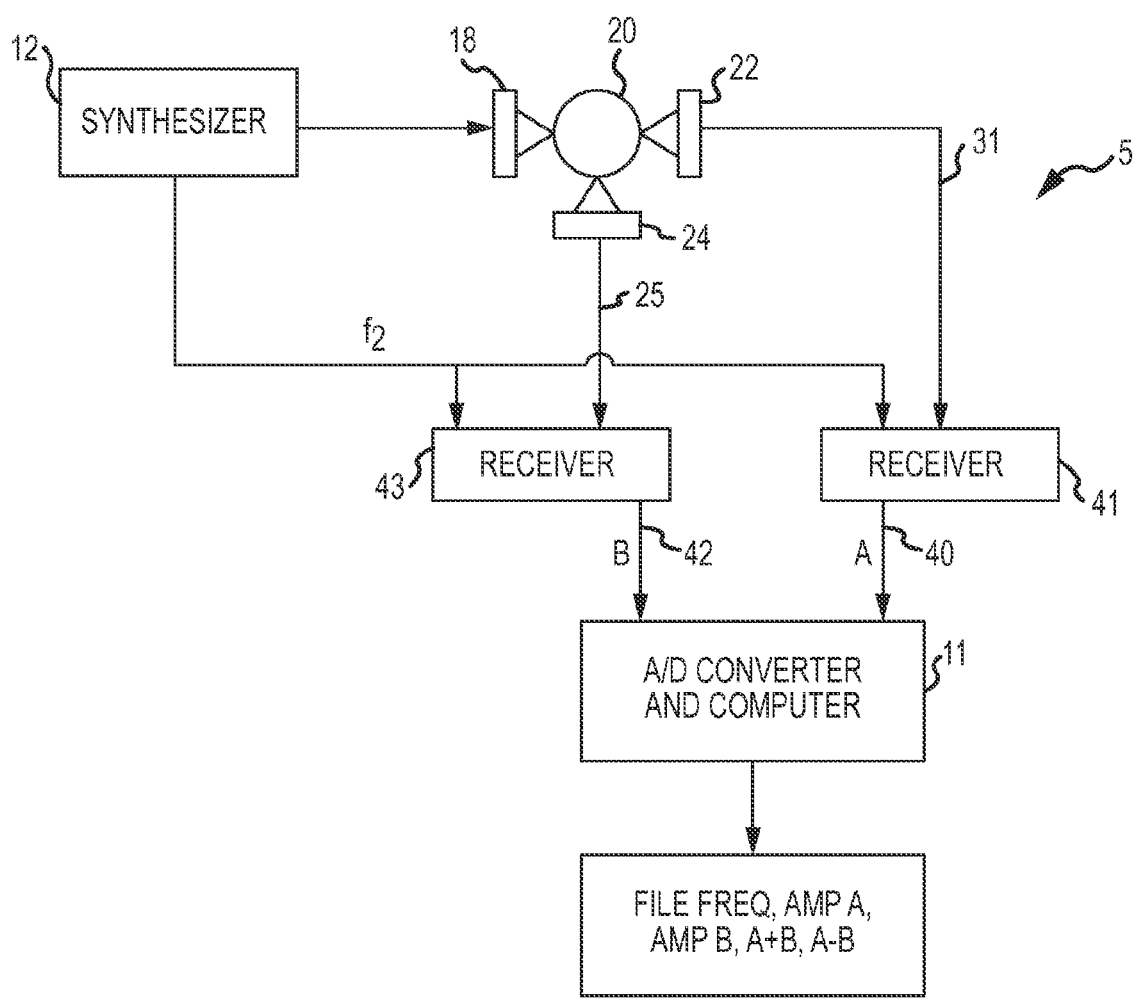
FIG. 2 shows a simplified block diagram of the resonance inspection tool of FIG. 1.

One embodiment of a resonance inspection tool or system (e.g., for accommodating resonant ultrasound spectroscopy measurement with a plurality of sensors; for process compensated resonance testing) is illustrated in FIGS. 1 and 2, and is identified by reference numeral 5. The resonance inspection tool 5 includes a computer 10 that provides for control of a synthesizer 12 and an analog to digital converter 11 for each data input channel connected to each receiving or response transducer 22, 24 of the resonance inspection tool 5. Transducer 22 has an output on line 31, while transducer 24 has an output on line 25.

Synthesizer 12 may have a frequency range from greater than 0 to 20 M Hertz. Other frequency ranges may be appropriate. Synthesizer 12 provides two outputs which are the frequency F1 at output 14 and a second output which is the frequency F2 at line 16. In one embodiment, the frequency F2 is either F1 plus a constant frequency such as 1000 Hertz for heterodyne operation of the receiver, or at F1 for homodyne operation. A first transducer 18 (e.g., the input or driving transducer) is excited at a frequency F1 by synthesizer 12. Transducer 18 provides vibration (e.g., ultrasonic) to an object 20 to be tested via resonance inspection.

The response of the object 20 is then received by two separate output transducers 22 and 24. The circuitry from the output transducer 22 and A/D converter 11 can be identical to circuitry between output transducer 24 and ND converter 11. For this reason, only the circuitry between output transducer 22 and A/D converter 11 will be discussed below. The times one (.times.1) amplifier 26 is connected to the output transducer 22, provides current for transformer 28, and has a feedback 27.

The output of transducer 22 is connected to a receiver 41 (FIG. 2). Receiver 41 is used for the purpose of providing amplification and noise rejection in the circuit between output transducer 22 and A/D converter 11. The output A (line 40) is applied to the A/D converter 11 within the computer 10. The A/D converter 11 provides an A/D conversion for each of lines 40 and 42. The converted information is then entered into a file which consists of the measured frequency, the amplitude of A, the amplitude of B, the amplitude of A plus B, and the amplitude of A minus B. This file is then used for further analysis of the spectrum to determine characteristics of a part 20 being tested.

The times one (.times.1) amplifier 26 provides feedback to an inner coaxial cable shield 30 which surround the lead from transducer 22 to amplifier 26. Shield 30 is another grounded shield which can also be used for noise suppression. The outer surrounding coaxial cable is not shown in FIG. 1. If lead 31 is short, the shield 30 may be omitted because capacitance will not be too large. The purpose of the inner shield 30 is to provide a cancellation of capacitance of the lead 31.

The transformer 28 may be a 4:1 step-down transformer used for impedance matching to the input of amplifier 32. In this regard, it should be noted that the output impedance of amplifier 26 may be much lower than the output impedance of transducer 22. This provides for the power gain and the necessary feedback to shield 30. The amplifier 32 may have a gain factor of 100:1 or a 40 db gain. Other gain factors may be appropriate. The amplifier 26 may be a broad-band amplifier having a band pass on the order of 50 M Hertz.

Mixer 34 has an output signal (e.g., a 1 K Hertz signal) having a magnitude which is proportional to the magnitude of the frequency F1 provided on line 14 from synthesizer 12. The function of the synthesizer 12 is to provide a point-by-point multiplication of instantaneous values of inputs on lines 16 and 33. The mixer 34 also has many high frequency output components which are of no interest. The high frequency components are therefore filtered out by the low-band pass filter 38 which is connected to mixer 34 by line 36. Filter 38 serves to clean-up the signal from mixer 34 and provide a voltage on line 40 which is only the output signal at an amplitude which is proportional to the amplitude of the output 31 of transducer 22.

Operation of the resonance inspection tool 5 will be briefly described in relation to measurement steps performed by measurement of the output of either transducer 22 or transducer 24 controlled by computer 10. A measurement cycle may be initiated, and provides initialization for the frequency F and the desired frequency step. The frequency step may be 1 Hertz or any other frequency selected for the measurement. Although a constant frequency step may be utilized, the frequency step may be determined by any appropriate algorithm. In one embodiment, the frequency step is determined by determining the start frequency and the stop frequency, and dividing the frequency difference by the number of steps desired for the measurement. In any case, the synthesizer 12 is configured to provide a plurality of input or drive frequencies to transducer 18.

Once a signal is picked up by the receiver (i.e., an output on line 33), a pause for ring delay there is a provided. The pause for ring delay may be on the order of 30 milliseconds, although other ring delays can be used if the object under test 20 has resonances that are narrower than a few Hertz. The purpose of the pause is to give the object 20 an opportunity to reach its steady state magnitude in response to a steady input from transducer 18. The pause time is time after the frequency is applied and before detection is initiated.

After the ring delay is complete, analog-to-digital converter 11 provides an output that can be used by the data recording computer. The output of the A/D conversion is then written to a file by the computer 10 for the purpose of analysis of the data by another program. Data comprising the unique signature or characterizing of the object 20 is written into file as it is created. Reading may be stopped when a read frequency is present and step 66 stops the program. Once information is entered into file, subsequent processing can be used to generate a signature or characterize the object 20 such as the resonant magnitudes, the sum of resonant magnitudes, the difference of resonant magnitudes, or other manipulations of the multiple channel multiple frequency measurement which is used to perform the unique signature of the object 20. The magnitude of the outputs at each sensor location for each resonance frequency may be compared.

Figure 3:
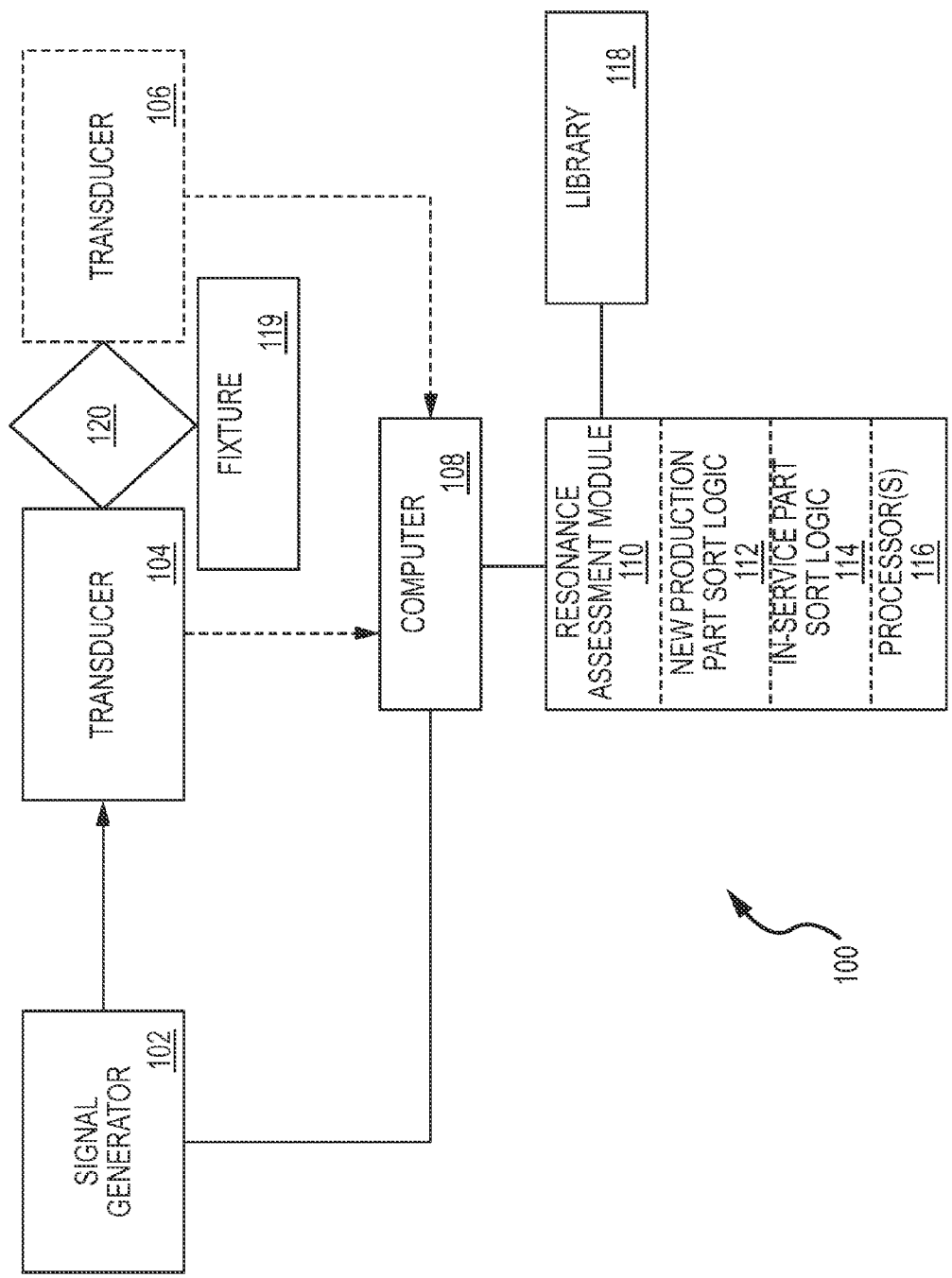
FIG. 3 is a block-diagram of another embodiment of a resonance inspection tool.

Another embodiment of a resonance inspection tool or system is illustrated in FIG. 3 and is identified by reference numeral 100. The resonance inspection tool 100 may be used to assess a part or part-under-test 120. This part 120 may be retained in a fixture 119 in any appropriate manner for execution of a resonance inspection.

The resonance inspection tool 100 includes a signal generator 102 of any appropriate type, at least one transducer (e.g., transducer 104), and a computer 108. The transducer 104 may be of any appropriate type. In one embodiment, the transducer 104 is in physical contact with the part 120 throughout execution of the inspection of the part 120, and in this case may be characterized as being part of the fixture 119 for the part 120. Another embodiment has the transducer 104 being maintained in spaced relation to the part 120 throughout execution of the resonance inspection of the part 120 (e.g., a laser, such as Nd:YAG lasers, TEA $CO_2$ lasers, excimer lasers, or diode lasers).

The computer 108 may include what may be characterized as a resonance assessment module 110. Generally, the resonance assessment module 110 may be configured to evaluate the results of a resonance inspection, for instance for purposes of determining whether the part 120 should be accepted or rejected by the resonance inspection tool 100, determining whether the part 120 is at an end-of-life state or condition, or the like. A part 120 that is "accepted" by the resonance inspection tool 100 may mean that the resonance inspection tool 100 has determined that the part 120 may be put into service (e.g., utilized for its intended purpose(s) and/or used according to its design specifications). In one embodiment, a part 120 that has been accepted by the resonance inspection tool 100 means that the tool 100 has determined that the part 120 is free of defects, is not in an end-of-life condition or state, is aging normally, or any combination thereof. A part 120 that is "rejected" by the resonance inspection tool 100 may mean that the resonance inspection tool 100 has determined that the part 120 should not be put into service (e.g., should not be utilized for its intended purpose(s) and/or should no longer be used according to its design specifications). In one embodiment, a part 120 that has been rejected by the resonance inspection tool 100 means that the tool 100 has determined that the part 120 includes at least one defect, is at or near an end-of-life condition or state, is aging abnormally, or any combination thereof.

A part 120 that is analyzed or assessed by the resonance inspection tool 100 may be of any appropriate size, shape, configuration, type, and/or class. For purposes of the resonance inspection tool 100, there could be two part classes. One part class includes new production parts—newly manufactured parts that have not yet been released from production (e.g., parts that have not been shipped for use by an end user or customer). New production parts include parts that may have undergone at least some post-production testing of any appropriate type (including without limitation a resonance inspection). Another part class includes in-service parts—parts that have been released from production for use in one or more end-use applications. An "in-service part" in the context of the embodiments to be addressed herein encompasses a part that has been used to at least some extent after having been released by the manufacturer. An in-service part may be a part that has been put into use by a party other than the manufacturer (e.g., a customer or end user). Although an in-service part could be used autonomously or independently of any other parts, an in-service part also may be incorporated by an assembly or system (e.g., a turbine blade (an in-service part) in a jet engine (an assembly or system)).

The signal generator 102 generates signals that are directed to the transducer 104 for transmission to the part 120 in any appropriate manner/fashion (e.g., via physical contact between the transducer 104 and the part 120; through a space between the transducer 104 and the part 120). Signals provided to the transducer 104 by the signal generator 102 are used to mechanically excite the part 120 (e.g., to provide energy to the part 120 for purposes of inducing vibration). Multiple frequencies may be input to the part 120 through the transducer 104 in any appropriate manner. This may be characterized as "sweeping" through a range of frequencies that are each input to the part 120, and this may be done in any appropriate manner for purposes of the resonance inspection tool 100. Any appropriate number/range of frequencies may be utilized, and any appropriate way of progressing through a plurality of frequencies (e.g., a frequency range) may be utilized by the resonance inspection tool 100.

In one embodiment, at least one other transducer 106 is utilized in the resonance inspection of the part 120 using the resonance inspection tool 100 of FIG. 3, including where two transducers 106 are utilized (e.g., in accordance with the embodiment of FIGS. 1 and 2 noted above). Each of the transducers 106, as well as the input or drive transducer 104, may be in physical contact with the part 120. It may be such that the part 120 is in fact entirely supported by the transducer 104 and any additional transducers 106 (e.g., the drive transducer 104 and one or more receive transducers 106 may define the fixture 119). Each transducer 106 that is utilized by the resonance inspection tool 100 is used to acquire the frequency response of the part 120 to the frequencies input to the part 120 by the drive transducer 104, and therefore each transducer 106 may be characterized as an output or receiver transducer 106.

One or more transducers 106 utilized by the resonance inspection tool 100 may be maintained in physical contact with the part 120 throughout the resonance inspection. Another option is for one or more of the transducers 106 to be maintained in spaced relation with the part 120 throughout the resonance inspection. A transducer 106 in the form of a laser may be maintained in spaced relation with the part throughout the resonance inspection, and may be utilized to obtain the frequency response of the part 120. Representative lasers that may be utilized as a transducer 106 by the resonance inspection system 100 include without limitation Nd:YAG lasers, TEA $CO_2$ lasers, excimer lasers, or diode lasers. In one embodiment, the frequency response of the part 120 is acquired by laser vibrometry utilizing at least one transducer 106. A given transducer 106 in the form of a laser may acquire resonance data on the part 120 from a single location, or a given transducer 106 in the form of a laser could acquire resonance data on the part 120 by scanning the laser over multiple locations on the part 120.

Another embodiment of the resonance inspection tool 100 of FIG. 3 utilizes only the transducer 104. That is, no additional transducers 106 are utilized by the resonance inspection tool 100 in this case, and therefore the transducer 106 is presented by dashed lines in FIG. 3. In this case, the transducer 104 is used to input a drive signal to the part 120 (e.g., to excite the part 120 at a plurality of different frequencies), and is also used to acquire the frequency response of the part 120 to these input drive frequencies. Representative configurations for this drive/receive transducer configuration 104 include without limitation piezoceramic, piezocomposites, piezoelectric quartz crystal, and other electromechanical materials.

In the above-noted drive/receive transducer configuration 106, a first drive signal at a first frequency (from the signal generator 102) may be transmitted to the part 120 through the transducer 104, the transmission of this first drive signal may be terminated, and the transducer 104 may be used to acquire a first frequency response of the part 120 to this first drive signal (including while a drive signal is being transmitted to the part 120). The signal generator 102 may also be used provide a second drive signal at a second frequency to the transducer 104, which in turn transmits the second drive signal to the part 120, the transmission of this second drive signal may be terminated, and the transducer 104 may once again be used to acquire a second frequency response of the part 120 to this second drive signal (including while a drive signal is being transmitted to the part 120). This may be repeated any appropriate number of times and utilizing any appropriate number of frequencies and frequency values. One or more drive signals may be sequentially transmitted to the part 120 by the signal generator 102 and transducer 104, one or more drive signals may be simultaneously transmitted to the part 120 by the signal generator 102 and transducer 104, or any combination thereof.

The frequency response of the part 120 is transmitted to the computer 108 of the resonance inspection tool 100 of FIG. 3. This computer 108 may be of any appropriate type and/or configuration, and is used by the resonance inspection tool 100 to evaluate the part 120 in at least some fashion (e.g., to determine whether to accept or reject the part 120). Generally, the part 120 is vibrated by the transducer 104 according to a predetermined signal(s), and the part 120 is evaluated by the resulting vibrational (e.g., whole body) response of the part 120. For instance, this evaluation may entail assessing the part 120 for one or more defects of various types, assessing whether the part 120 is at or near the end of its useful, life, assessing whether the part 120 is aging normally or abnormally, or any combination thereof.

The computer 108 may incorporate and utilize the above-noted resonance assessment module 110 to evaluate the response of the part 120 to a resonance inspection. The resonance assessment module 110 may be of any appropriate configuration and may be implemented in any appropriate manner. In one embodiment, the resonance assessment module 110 includes at least one new production part sort logic 112 (e.g., logic configured to determine whether to accept or reject new production parts), at least one in-service part sort logic 114 (e.g., logic configured to determine whether to accept or reject in-service parts), along with one or more processors 116 of any appropriate type and which may be implemented in any appropriate processing architecture. The assessment of the response of the part 120 to the input drive signals may entail comparing the response to a library 118 utilized by the resonance inspection tool 100. This library 118 may be stored on a computer-readable storage medium of any appropriate type or types, including without limitation by using one or more data storage devices of any appropriate type and utilizing any appropriate data storage architecture.

Figure 4:
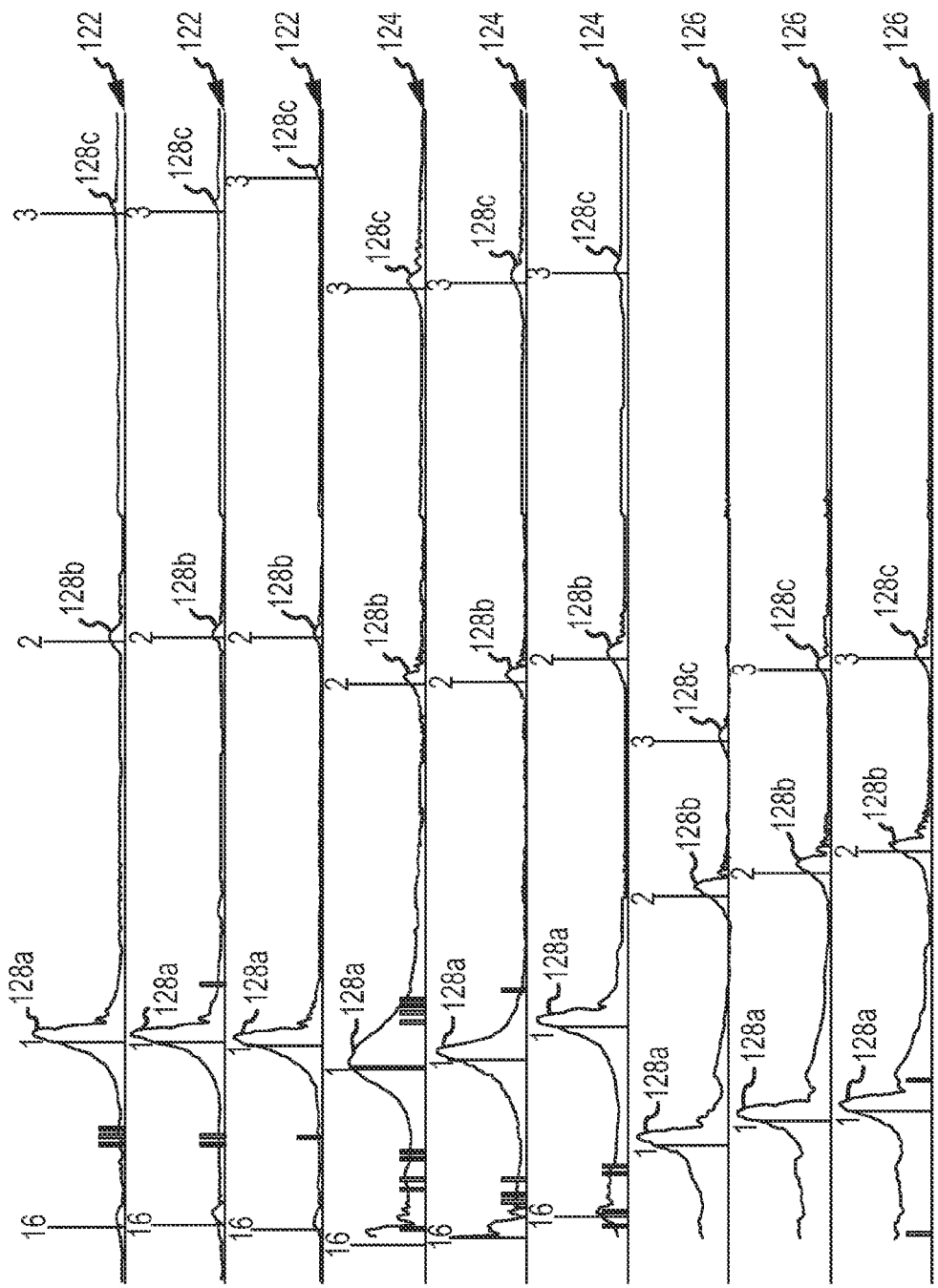
FIG. 4 presents various resonance inspection results of parts that may be included in the library utilized by the resonance inspection tool of FIG. 3.

The library 118 of the resonance inspection tool 100 may include various types of resonance inspection results to allow the resonance inspection tool 100 to assess a part 120. Generally, the resonance inspection results from the part 120 are compared with data in the library 118 from at least one other part that is the same as the part 120 in one or more respects (e.g., a part 120 in the form of a turbine blade will be compared to turbine blade data in the library 118; a part 120 in the form of a turbine blade will not be compared with ball bearing data in the library 118). Representative resonance inspection results are presented in FIG. 4, and are of a type that may be included in the library 118. The three spectra 122 shown in FIG. 4 represent the frequency response of a new production part 120 to a certain input frequency, and where this new production part 120 has been accepted by the resonance inspection tool 100. Note how the three peaks 128a, 128b, and 128c differ in at least one respect between the various spectra 122, but yet the corresponding new production part 120 is acceptable in all three instances.

The three spectra 124 shown in FIG. 4 represent the frequency response of an in-service production part 120 to a certain input frequency, and where this in-service part 120 has been accepted by the resonance inspection tool 100. Note how the three peaks 128a, 128b, and 128c in the spectra 124 differ in at least one respect from the corresponding peaks 128a, 128b, and 128c in the spectra 122 (again, associated with a new production part 120).

The three spectra 126 shown in FIG. 4 represent the frequency response of an in-service production part 120 to a certain input frequency, and where this in-service part 120 has been rejected by the resonance inspection tool 100. Note how the three peaks 128a, 128b, and 128c in the spectra 126 differ in at least one respect from the corresponding peaks 128a, 128b, and 128c in the spectra 124 (again, associated with an in-service part 120 that the resonance inspection tool 100 would accept). Generally, each of the peaks 128a, 128b, and 128c in the spectra 126 has shifted to the left compared to the corresponding peaks 128a, 128b, and 128c in the spectra 122 and 124. Moreover, note the "compression" between the peaks 128a, 128b in the spectra 126 compared to the spectra 122, 124, as well as the "compression" between the peaks 128b, 128c in the spectra 126 compared to the spectra 122, 124.

Figure 5:
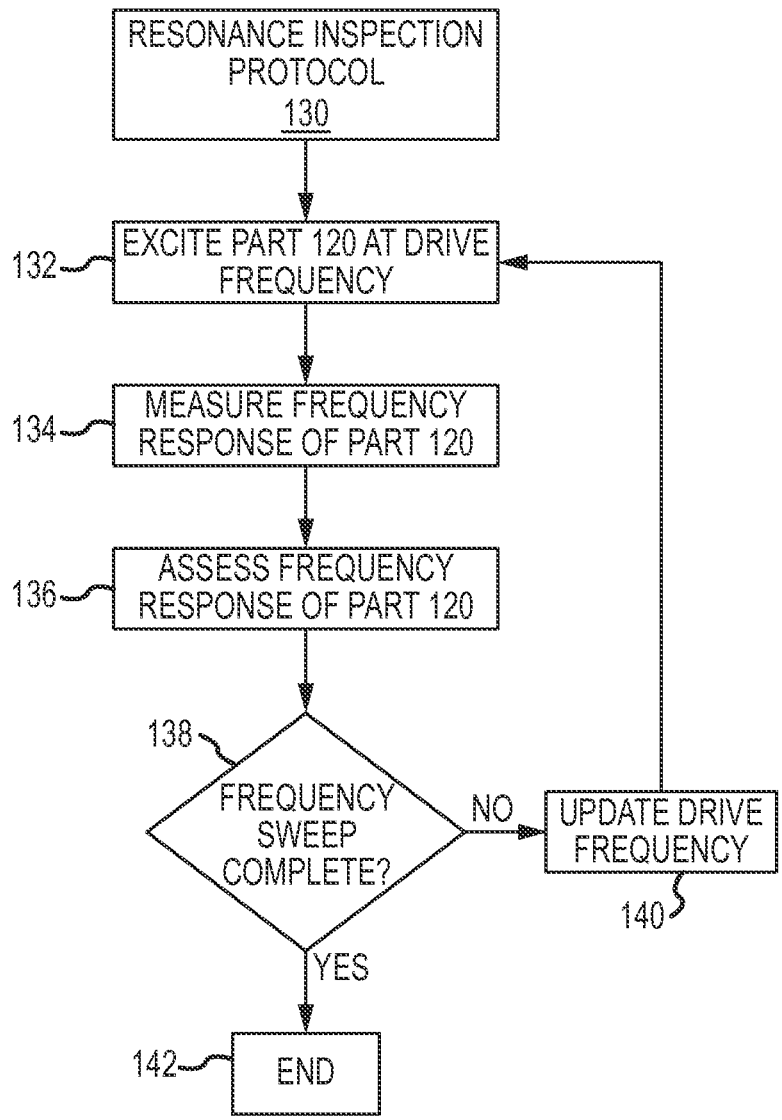
FIG. 5 is one embodiment of a resonance inspection protocol that may be utilized by a resonance inspection tool.

One embodiment of a resonance inspection protocol that may be utilized by the resonance inspection tool 100 of FIG. 3 is presented in FIG. 5 and is identified by reference numeral 130. Step 132 of the resonance inspection protocol 130 is directed to exciting a part 120 at a drive frequency (e.g. via a signal from the signal generator 102 that is input to the part 120 through the transducer 104). The response of the part 120 is obtained or measured pursuant to step 134 (e.g., via one or more transducers 106; via the transducer 104 in a single transducer configuration). It should be appreciated that steps 132 and 134 may be executed in at least partially overlapping relation (e.g., the frequency response of the part 120 could be obtained as a drive signal is being applied to the part 120), although steps 132 and 134 could be sequentially executed as well.

The frequency response of the part 120 is assessed pursuant to step 136 of the resonance inspection protocol 130. Step 138 of the protocol 130 is directed to determining if the frequency sweep is complete—whether each of the desired drive frequencies has been input to the part 120. If not, the protocol 130 proceeds to step 140, and which is directed to updating or changing the drive frequency to be input to the part 120. Control is then returned to step 132 of the protocol 130 for repetition in accordance with the foregoing. Once the part 120 has been driven at each of the desired frequencies, the protocol 130 may be terminated pursuant to step 142.

Step 136 of the resonance inspection protocol 130 is again directed to assessing the response (e.g., frequency; whole body) of the part 120 (e.g., using the sort logic 112 or 114 and/or comparing the response of the part 120 to the library 118 of the resonance inspection tool 100). This assessment may be undertaken at any appropriate time and in any appropriate manner. For instance, the assessment associated with step 136 could be undertaken while the part 120 continues to be driven by a signal at one or more frequencies. Another option is for the assessment provided by step 136 to be undertaken only after all drive signals have been input to the part 120 (step 132), after the all frequency responses have been obtained (step 134), or both.

Figure 6:
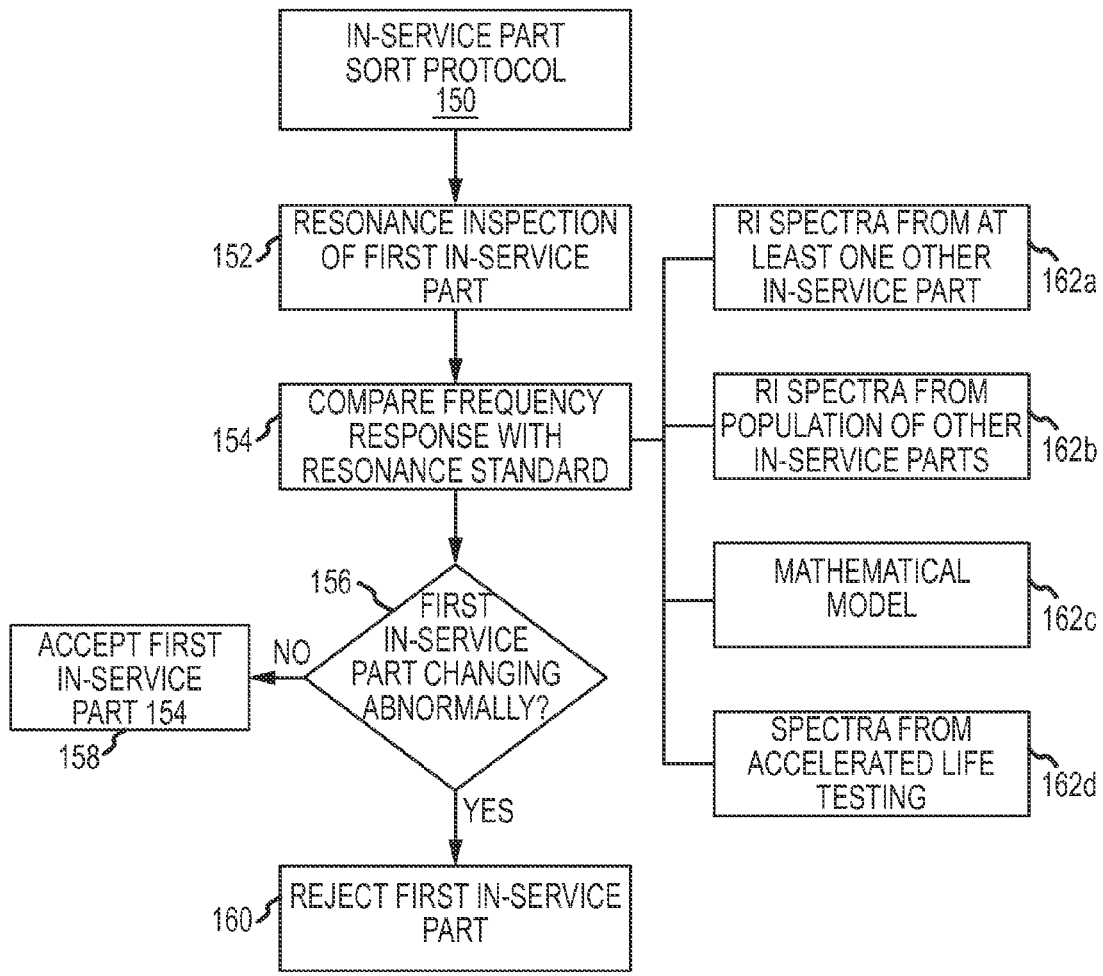
FIG. 6 is one embodiment of a sort protocol for in-service parts that may be utilized by a resonance inspection tool.

One embodiment of a sort protocol for in-service parts is presented in FIG. 6 and is identified by reference numeral 150. The sort protocol 150 may be utilized by the in-service part sort logic 114 of the resonance inspection tool 100 shown in FIG. 3, and is configured for the assessment of in-service parts. Generally, the sort protocol 150 is directed to determining whether or not an in-service part is experiencing normal changes while in service. Stated another way, the sort protocol 150 may be characterized as being directed to determining whether an in-service part is aging normally or abnormally and via a resonance inspection. Each resonance inspection of an in-service part may be conducted while the in-service part remains in an installed state or condition (e.g., in situ) for purposes of the sort protocol 150. Alternatively, each resonance inspection of an in-service part may be conducted with the in-service part being in an uninstalled state or condition (e.g., after having been removed from an assembly incorporating the same) for purposes of the sort protocol 150.

A resonance inspection of a first in-service part (e.g., part 120 shown in FIG. 3) is conducted pursuant to step 152 of the sort protocol 150 of FIG. 6 (e.g., via execution of the resonance inspection protocol 130 of FIG. 5). The frequency response of the first in-service part is compared with a resonance standard pursuant to step 154. This "resonance standard" may be incorporated by the library 118 used by the resonance inspection tool 100 (FIG. 3) and/or may be utilized by the in-service part sort logic 114, and in any case may characterize or define what should be a "normal change" for a predetermined in-service part (e.g., to determine whether the first in-service part is changing or aging in a normal manner or fashion). That is, the comparison of step 154 is undertaken for purposes of determining whether the first in-service part is changing normally or abnormally (step 156). If the comparison with the resonance standard (step 154) determines that the first in-service part is changing abnormally, the sort protocol 150 proceeds from step 156 to step 160. A first in-service part that is changing abnormally may be rejected by the sort protocol 150 pursuant to step 160 (e.g., the first in-service part may be designated to be taken out of service). A first in-service part that is changing normally is accepted by the sort protocol 150 pursuant to step 158 (e.g., the first in-service part may be returned to service).

The resonance standard associated with step 154 may include actual and/or projected/predicted resonance inspection results. Moreover, these resonance inspection results may be from various points in time over the life cycle of a part (e.g., resonance inspection results when in the form of a new production part, resonance inspection results at or associated with 5,000 cycles of usage, resonance inspection results at or associated with 10,000 cycles of usage, resonance inspection results at or associated with 15,000 cycles of usage, and so forth). Step 156 of the sort protocol 150 may or may not take usage data (e.g., hours or cycles of operation) into account when assessing a particular in-service part. For instance, step 156 could be configured so that resonance inspection results from the in-service part being assessed via the sort protocol 150 would have to "match" data in the resonance standard having the same or comparable usage data (e.g., if the in-service part that was being assessed via the sort protocol 150 was at 10,000 cycles of usage, step 156 could be configured such that resonance inspection results from this in-service part would have to match data in the resonance standard that are also associated with 10,000 cycles of usage). Step 156 could also be configured so that resonance inspection results from the in-service part being assessed via the sort protocol 150 would only need to "match" data in the resonance standard, regardless of any associated usage data (e.g., step 156 could be configured to determine that a part at 10,000 cycles was changing normally, even though its resonance inspection results "matched" data in the resonance standard that was in fact associated with 20,000 cycles).

The resonance standard associated with step 154 of the sort protocol 150 of FIG. 6 may be of various forms. Representative resonance standards are shown in FIG. 6. The resonance standard for step 154 may be in the form of: 1) spectra from one or more other in-service parts (e.g., spectra from a resonance inspection previously conducted on one or more in-service parts other than that being inspected pursuant to the sort protocol 150 (box 162a); 2) one or more spectra from a population of other in-service parts (box 162b); 3) resonance inspection results predicted and/or derived via mathematical modeling (box 162c); and 4) spectra obtained from accelerated life testing (box 162d).

The resonance standard associated with step 154 of the sort protocol 150 could be in the form of any one or more of the type of spectra 124 shown in FIG. 4 (e.g., box 162a). If the resonance inspection results from the resonance inspection conducted pursuant to step 152 matched or complied with any of these spectra 124 in one or more respects, the in-service part could be accepted by step 158 of the sort protocol 150.

The resonance standard used by step 154 of the sort protocol 150 may be based upon a population of in-service parts (box 162b). This population of in-service parts does not need to include the first in-service part that is being assessed via the sort protocol 150. The population of in-service parts may be viewed as a "peer group" for purposes of assessing the first in-service part via the sort protocol 150 (e.g., other parts manufactured in accordance with common specifications and/or that are functionally interchangeable with the first in-service part). For instance, the resonance standard may be in the form of spectra (e.g., spectra 124 from FIG. 4) from each of a plurality of in-service parts that are within the population. If the comparison of step 154 determines that the resonance inspection results from the first in-service part (step 152) match or comply with any of these spectra from the population in one or more respects, the first in-service part may be accepted pursuant to step 158 of the sort protocol 150. The resonance standard associated with step 154 may also be in the form of an average of spectra from each of a plurality of in-service parts that are within the noted population. If the comparison of step 154 determines that the resonance inspection results (step 152) match or comply with this spectral average from the population in one or more respects, the first in-service part may be accepted pursuant to step 158 of the sort protocol 150.

The resonance standard associated with step 154 of the sort protocol 150 may also be provided by mathematical modeling (box 162c). This mathematical modeling may be used to generate resonance inspection results for various times over the life of a part that is changing normally. If the comparison of step 154 determines that the resonance inspection results (step 152) match or comply with any of these mathematically derived resonance inspection results in one or more respects, the first in-service part may be accepted pursuant to step 158 of the sort protocol 150.

The resonance standard associated with step 154 of the sort protocol 150 may also be provided by accelerated life testing (box 162d). Resonance inspection results may be acquired as a part undergoes accelerated life testing, and these resonance inspection results may be used by the resonance standard associated with step 154. If the comparison of step 154 determines that the resonance inspection results (step 152) match or comply with any of the resonance inspection results acquired during the accelerated life testing in one or more respects, the first in-service part may be accepted pursuant to step 158 of the sort protocol 150.

Figure 7:
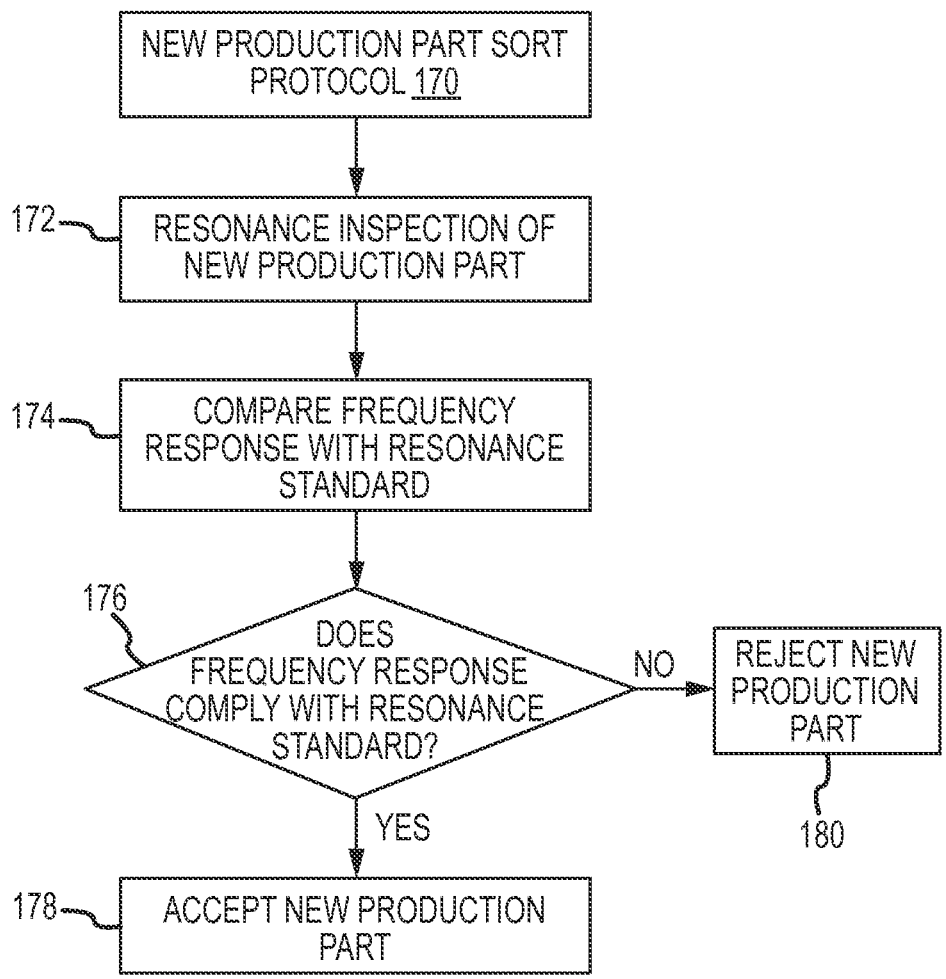
FIG. 7 is one embodiment of a sort protocol for new production parts that may be utilized by a resonance inspection tool.

One embodiment of a sort protocol for new production parts is presented in FIG. 7, is identified by reference numeral 170, and may be used by the resonance inspection tool 100 of FIG. 3. A resonance inspection of a new production part (e.g., part 120 shown in FIG. 3) is conducted pursuant to step 172 of the sort protocol 170 of FIG. 7 (e.g., via execution of the resonance inspection protocol 130 of FIG. 5). The frequency response of the new production part is compared with at least one resonance standard pursuant to step 174. Each such "resonance standard" may be incorporated by the library 118 used by the resonance inspection tool 100 (FIG. 3) and/or may be utilized by the new production part sort logic 112, and in any case may characterize or define what should be a "normal" new production part. That is, the comparison of step 174 is undertaken for purposes of determining whether the new production part is "normal" (step 176). A new production part that does not comply with the relevant resonance standard(s) may be rejected by the sort protocol 170 pursuant to step 180 (e.g., the new production part may be designated for scrapping). A new production part that complies with the relevant resonance standard(s) is accepted by the sort protocol 170 pursuant to step 178 (e.g., the new production part may be designated for service).

Both resonance data and surface vibration data may be utilized to evaluate a given part 120. One embodiment of a surface vibration inspection tool is presented in FIG. 8A and is identified by reference numeral 100'. The surface vibration inspection tool 100' may utilize the signal generator 102, drive transducer 104, fixture 119, and computer 108 discussed above in relation to the resonance inspection tool 100 of FIG. 3. The foregoing discussion of these components is thereby equally to the surface vibration inspection tool 100'.

Figure 8A:
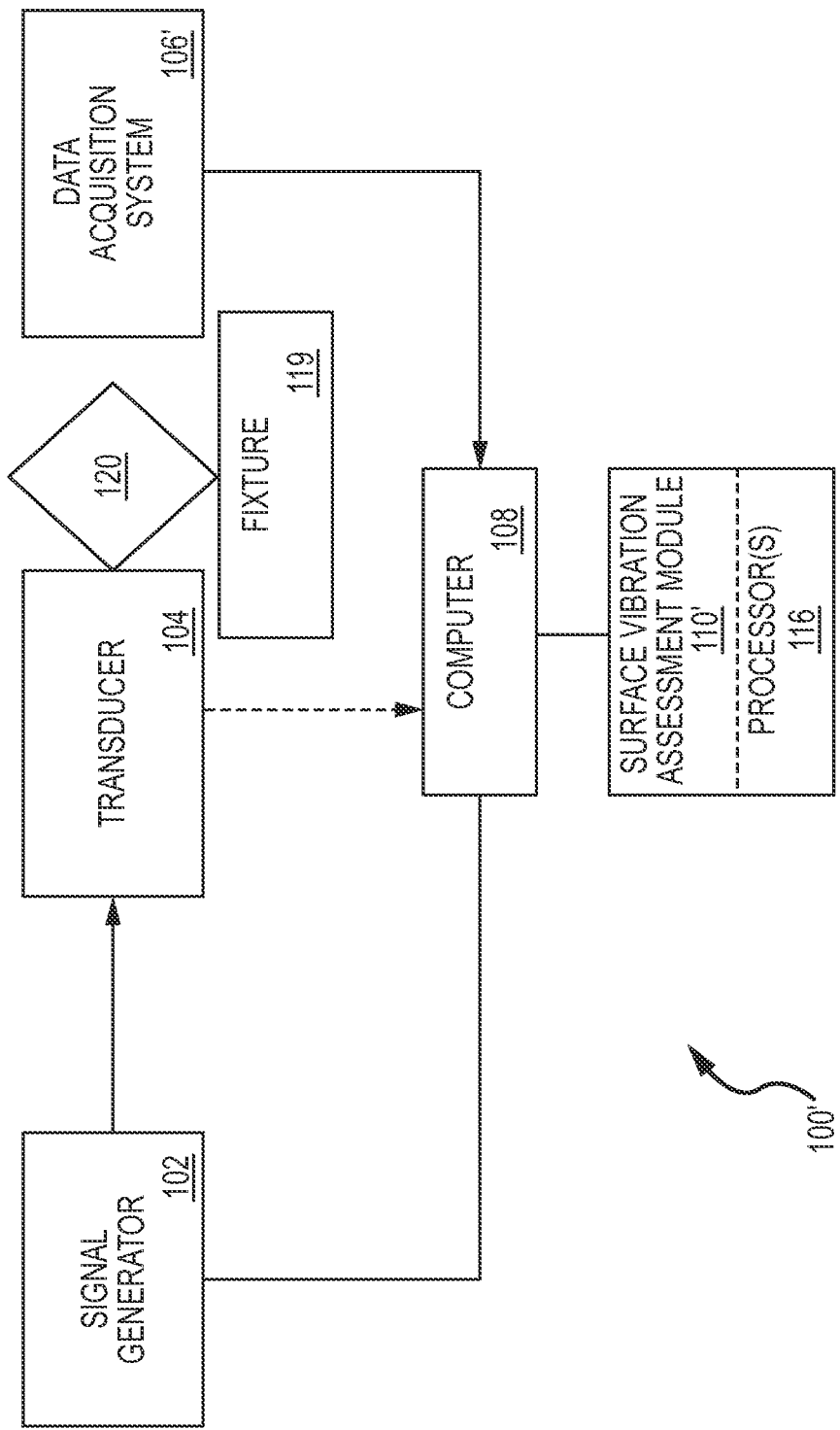
FIG. 8A is a block-diagram of one embodiment of a surface vibration inspection tool.

The surface vibration inspection tool 100' of FIG. 8A acquires surface vibration data utilizing what may be characterized as a data acquisition system 106'. The data acquisition system 106' may be of any appropriate configuration for acquiring surface vibration data from the part 120 (e.g., as excited by the transducer 104). Representative data recording systems 106' for the surface vibration inspection tool 100' include without limitation holographic interferometry, laser vibrometry, laser Doppler velocimetry, scanning laser vibrometry, and 2-d and 3-d scanning laser vibrometry.

The computer 108 used by the surface vibration inspection tool 100' of FIG. 8A may incorporate what may be characterized as a surface vibration assessment module 110' that utilizes one or more processors 116 arranged in any appropriate processing architecture. Surface vibration data provided to the computer 108 may be assessed in any appropriate manner by the surface vibration assessment module 110'. As should be appreciated by a review of the resonance inspection tool 100 of FIG. 3 and the surface vibration inspection tool 100' of FIG. 8A, the tools 100/100' could be combined into a single inspection tool if desired (e.g., although separate configurations may be used to acquire the resonance data and the surface vibration data in accordance with the various protocols that will now be described). In one embodiment, the part 120 is maintained in the fixture 119 for conducting both a resonance inspection and a surface vibration inspection of the part 120.

Figure 8B:
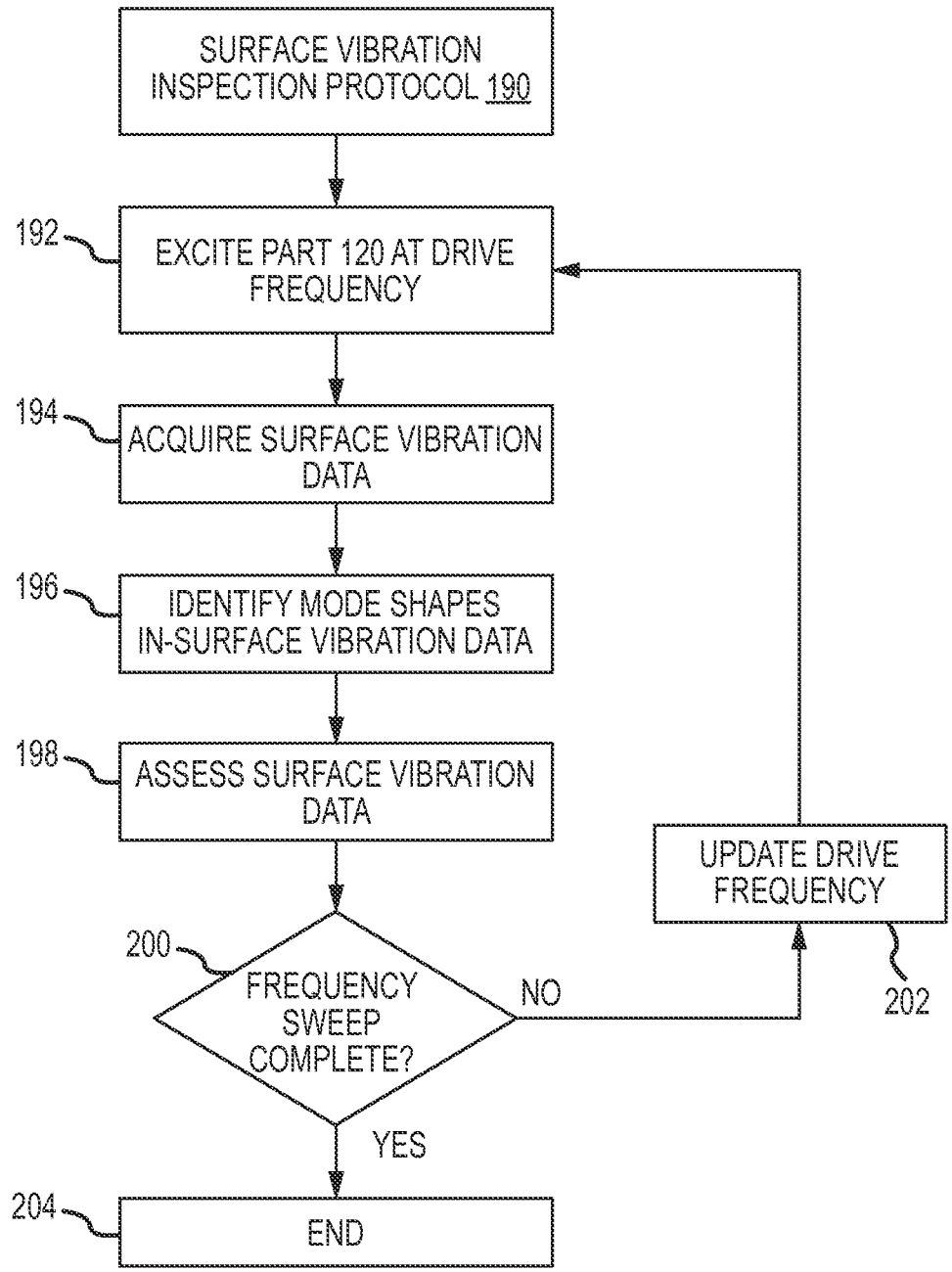
FIG. 8B is one embodiment of a surface vibration inspection protocol that may be utilized by a surface vibration inspection tool.
Figures 9E, 9F:
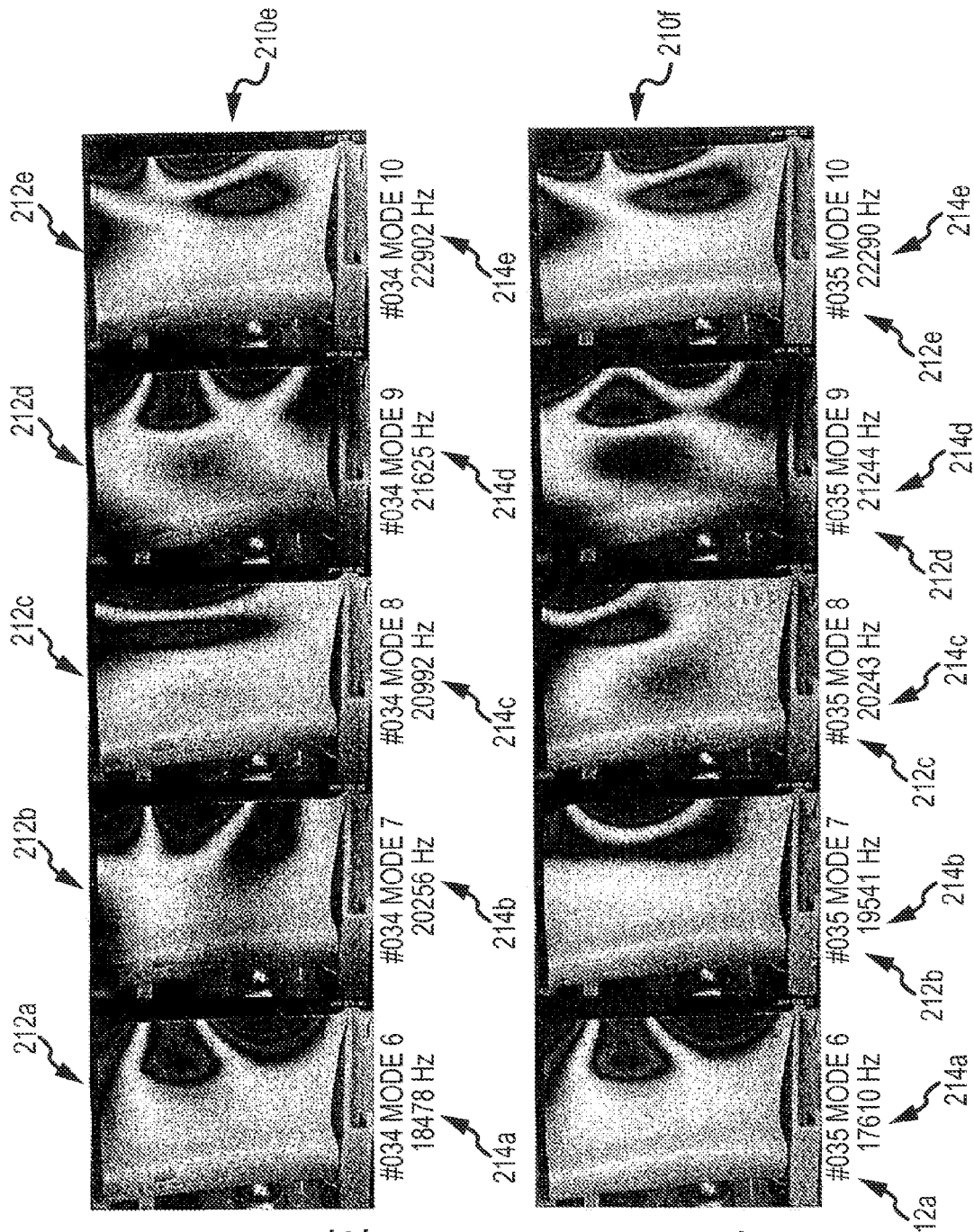
Figure 9I:
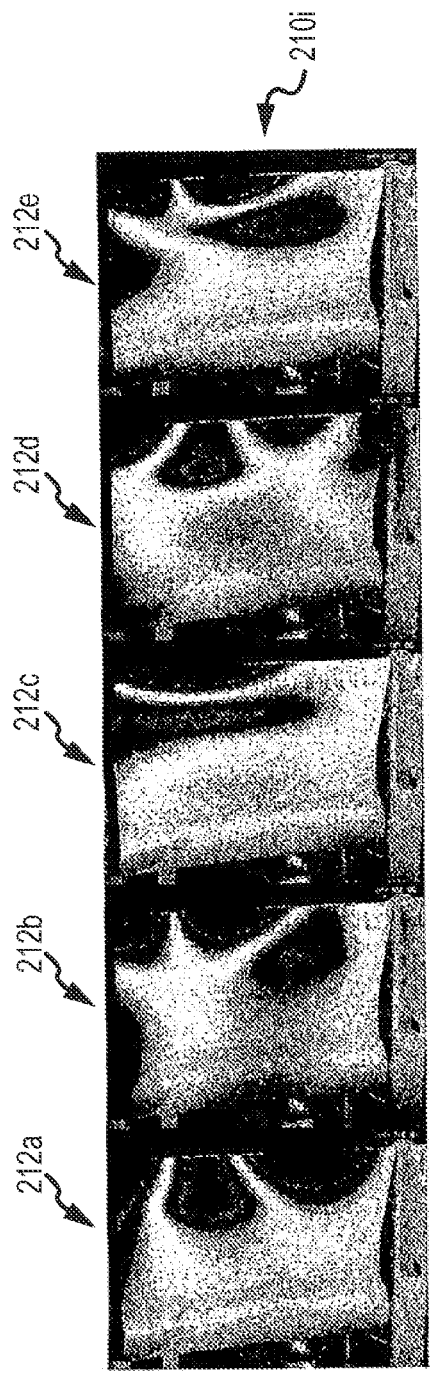
Figure 9J:
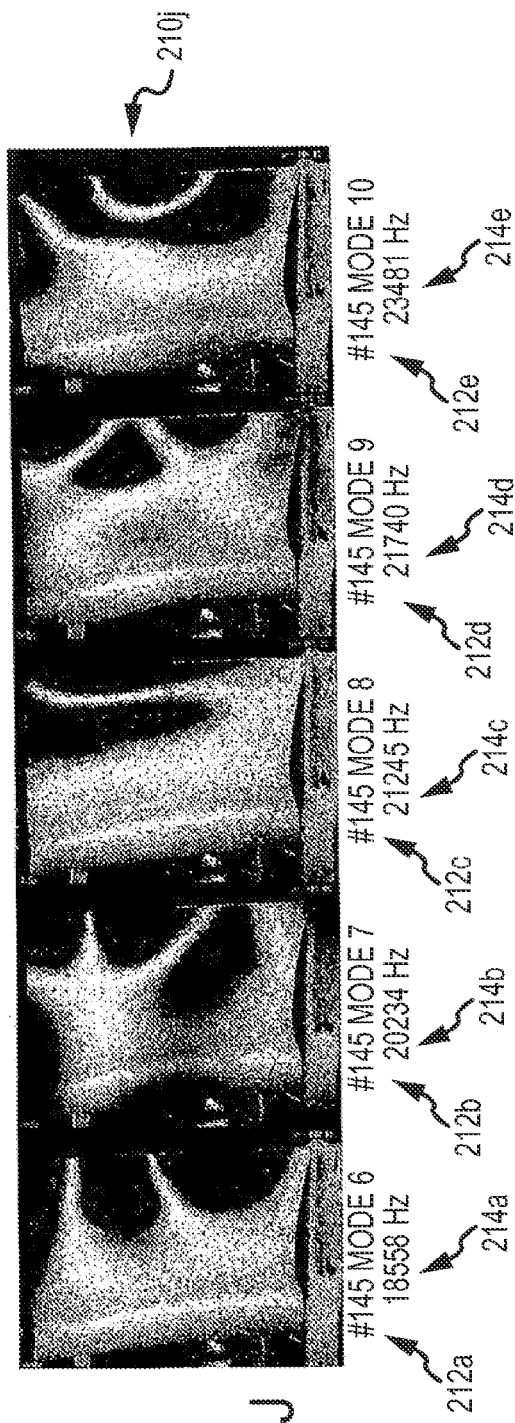

One embodiment of a surface vibration inspection protocol is presented in FIG. 8B, is identified by reference numeral 190, and may be utilized by the surface vibration inspection tool 100' of FIG. 8A. Step 192 of the surface vibration inspection protocol 190 is directed to exciting a part 120 at a drive frequency (e.g. via a signal from the signal generator 102 that is input to the part 120 through the transducer 104). The response of the part 120 is acquired pursuant to step 194. In the case of the surface vibration inspection protocol 190, this "response" is the acquisition of surface vibration data. This surface vibration data may be acquired in any appropriate manner, including as noted above in relation to the data acquisition system 106'.

The vibrational modes or mode shapes in the surface vibration data (step 194) may be identified in any appropriate manner pursuant to step 196 of the surface vibration inspection protocol 190 of FIG. 8B. Modeling, mathematical derivation, or the like may be utilized in the identification of the vibrational modes or mode shapes in the surface vibration data through execution of step 196. In any case and as will be discussed in more detail below in relation to FIGS. 9A-J, the identification of the vibrational modes or mode shapes in the surface vibration data (step 196) may be used to identify an associated frequency that may be utilized in at least some fashion by the resonance inspection tool 100 of FIG. 3 (e.g., for execution of the resonance inspection protocol 130 of FIG. 5).

Step 198 of the surface vibration inspection protocol 190 is directed to assessing the surface vibration data. This may be done in any appropriate manner, for instance by comparing the surface vibration data (step 194) to what may be characterized as at least one "surface vibration standard" (e.g., stored on a computer-readable storage medium of the computer 108). If the frequency sweep is not yet complete—if all of the desired drive frequencies have not yet been input to the part 120 for purposes of the surface vibration inspection protocol 190—the drive frequency is updated (step 202) and control is then returned to step 192 of the protocol 190 for repetition in accordance with the foregoing. Once the part 120 has been driven at each of the desired frequencies, the surface vibration inspection protocol 190 may be terminated pursuant to step 204.

As in the case of the resonance inspection protocol 130 of FIG. 5, all of the desired surface vibration data may be acquired (step 194) before the assessment of the same is undertaken (step 198). However, the surface vibration data may also be assessed (step 198) as the part 120 continues to be excited (step 192). The vibrational modes or mode shapes (step 196) may also be identified at any appropriate time, including after all of the desired surface vibration data has been acquired (step 194) or as surface vibration data continues to be acquired (step 194) during excitation of the part (step 192).

The surface vibration inspection protocol 190 of FIG. 8B may be executed simultaneously with the execution of the resonance inspection protocol 130 of FIG. 5. Therefore and for a given drive frequency being input to the part 120 (step 132 of the resonance inspection protocol 130 of FIG. 5; step 192 of the surface vibration inspection protocol 190 of FIG. 8B), both resonance data (step 134 of the resonance inspection protocol 130 of FIG. 5) and surface vibration data (step 194 of the surface vibration inspection protocol 190 of FIG. 8B) may be acquired. In this regard, the part 120 may be retained in a common fixture 119 for at least the data acquisition portions of each of the resonance inspection protocol 130 of FIG. 5 and the surface vibration inspection protocol 190 of FIG. 8B.

Representative surface vibration data is presented in FIGS. 9A-J, respectively, and may be acquired by step 194 when conducting the surface vibration inspection protocol 190 of FIG. 8B on a part 120. FIGS. 9A-J each present five (5) different vibrational modes or mode shapes 212a-e (also labeled as modes 6-10) for a given drive frequency 210a-j, along with the associated mode frequency 214a-e. For instance, and for the drive frequency 210a of FIG. 9A: there is a mode shape 212a (mode 6) and corresponding mode frequency 214a (18,485 Hz); there is a mode shape 212b (mode 7) and corresponding mode frequency 214b (20,202 Hz); there is a mode shape 212c (mode 8) and corresponding mode frequency 214c (20,989 Hz); there is a mode shape 212d (mode 9) and corresponding mode frequency 214d (21,835 Hz); and there is a mode shape 212e (mode 10) and corresponding mode frequency 214e (23,054 Hz).

Representative resonance data is presented in FIGS. 10A-J, respectively, and may be acquired by step 134 when conducting the resonance inspection protocol 130 of FIG. 5 on the same part 120 addressed by FIGS. 9A-J. Initially, FIGS. 10A-J present the resonance data 220a-j for the corresponding drive frequencies 210a-j of FIGS. 9A-J. The vibrational modes 212a-e from FIGS. 9A-J may be used to identify the vibrational modes or mode shapes 212a-e in the corresponding resonance data 220a-j of FIGS. 10A-J. Generally: 1) for the drive frequency 210a in FIG. 9A, the mode frequency 214a (18,485 Hz) associated with the vibrational mode 212a (mode 6) of the surface vibration data of FIG. 9A may be used to identify the corresponding resonance frequency peak 224a (18,506 Hz) in the resonance data 220a of FIG. 10A that should be associated with the vibrational mode 212a (mode 6); 2) for the drive frequency 210a in FIG. 9A, the mode frequency 214b (20,202 Hz) associated with the vibrational mode 212b (mode 7) of the surface vibration data of FIG. 9A may be used to identify the corresponding resonance frequency peak 224b (20,287 Hz) in the resonance data 220a of FIG. 10A that should be associated with the vibrational mode 212b (mode 7); 3) for the drive frequency 210a in FIG. 9A, the mode frequency 214c (20,989 Hz) associated with the vibrational mode 212c (mode 8) of the surface vibration data of FIG. 9A may be used to identify the corresponding resonance frequency peak 224c (21,011 Hz) in the resonance data 220a of FIG. 10A that should be associated with the vibrational mode 212c (mode 8); 4) for the drive frequency 210a in FIG. 9A, the mode frequency 214d (21,835 Hz) associated with the vibrational mode 212d (mode 9) of the surface vibration data of FIG. 9A may be used to identify the corresponding resonance frequency peak 224d (21,939 Hz) in the resonance data 220a of FIG. 10A that should be associated with the vibrational mode 212d (mode 9); and 5) for the drive frequency 210a in FIG. 9A, the mode frequency 214e (23,054 Hz) associated with the vibrational mode 212e (mode 10) of the surface vibration data of FIG. 9A may be used to identify the corresponding resonance frequency peak 224e (23,111 Hz) in the resonance data 220a of FIG. 10A that should be associated with the vibrational mode 212e (mode 10).

Figure 10A:
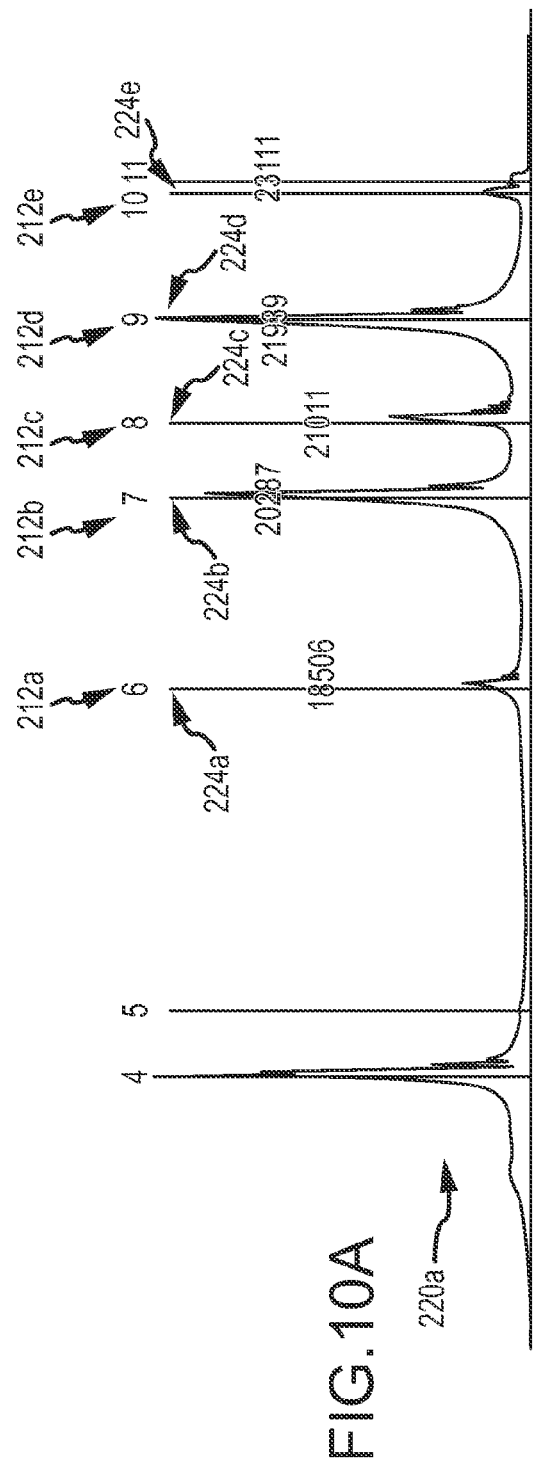
Figure 10B:
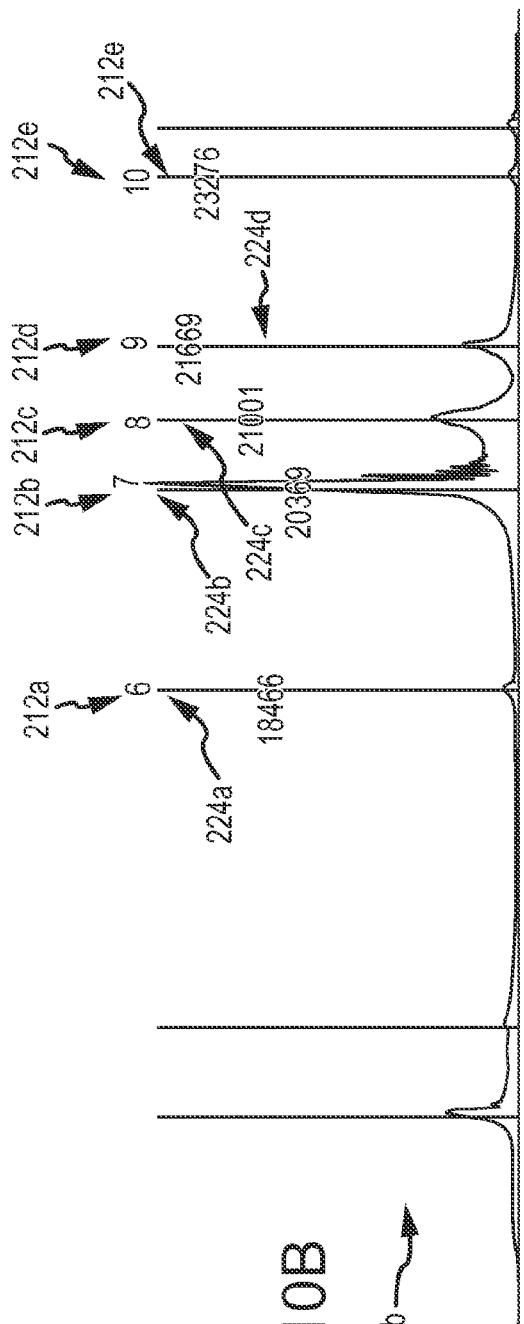
Figure 10C:
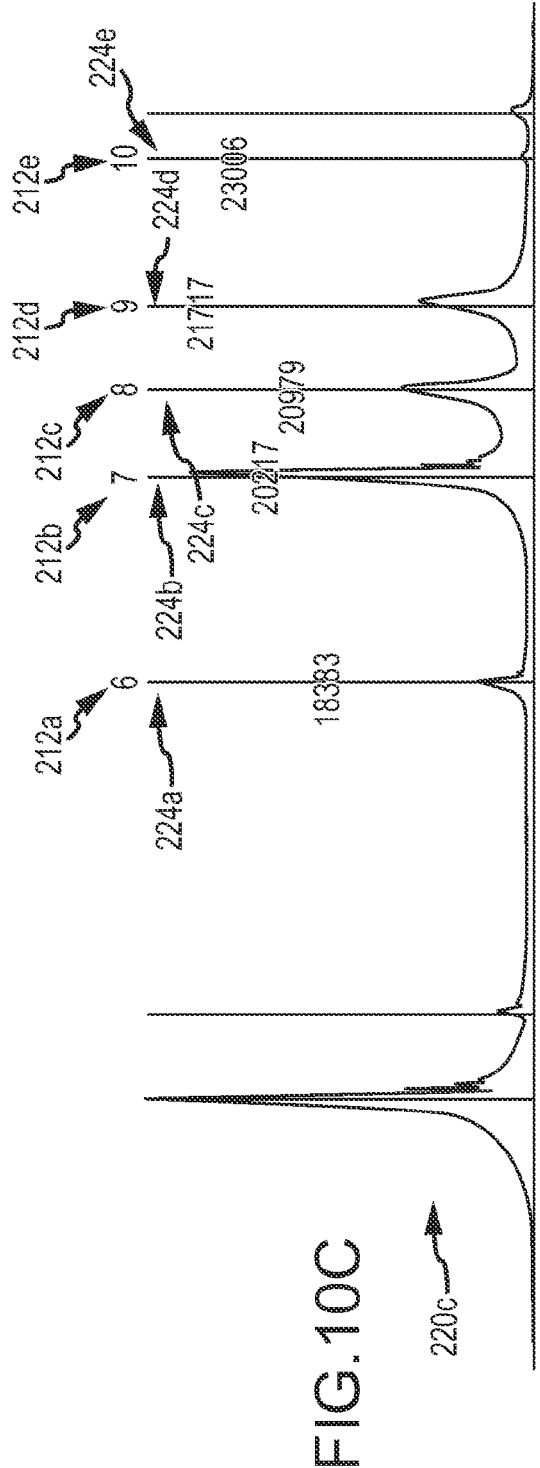
Figure 10D:
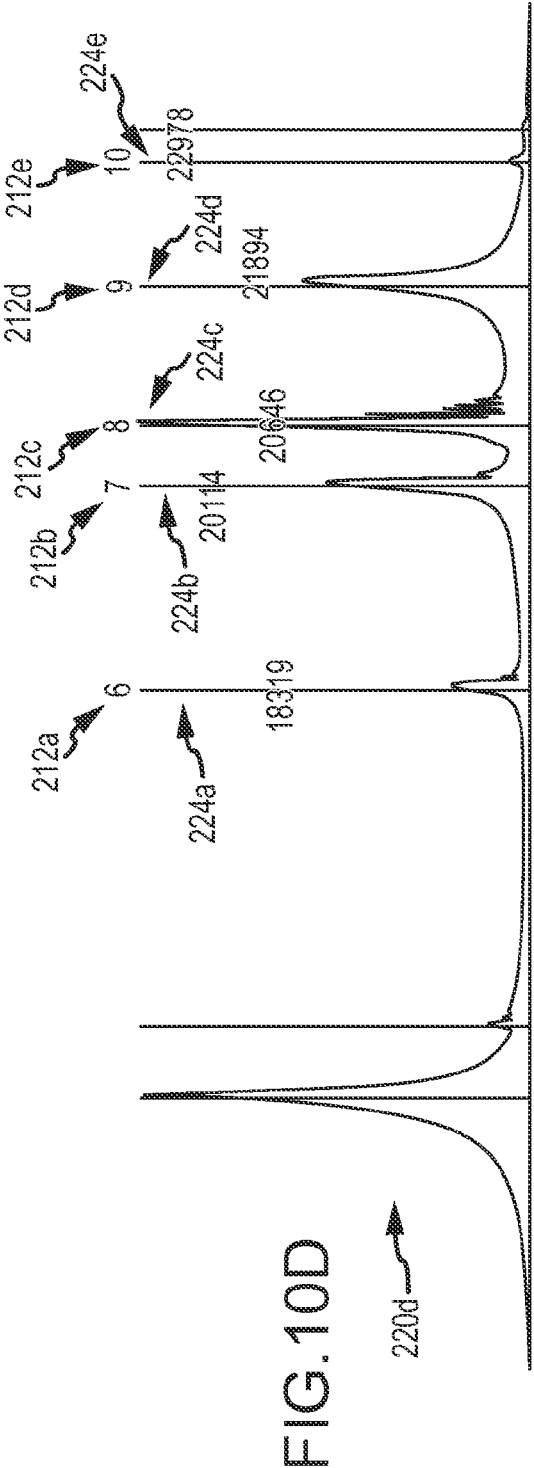
Figure 10E:
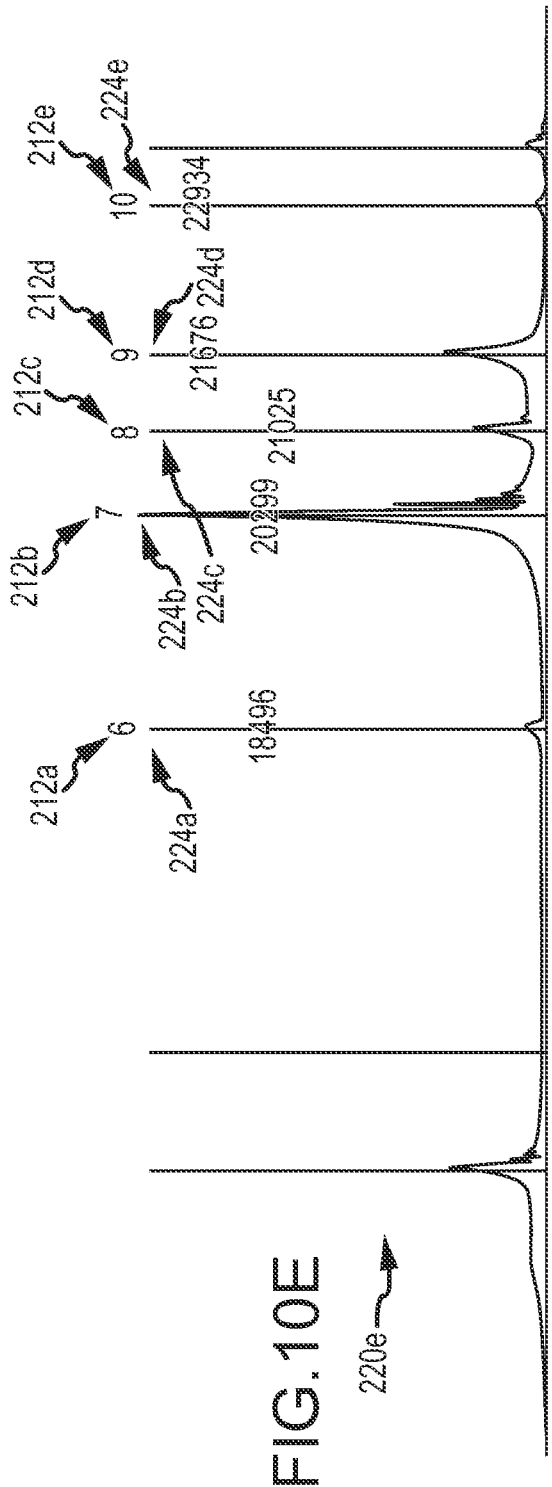
Figure 10F:
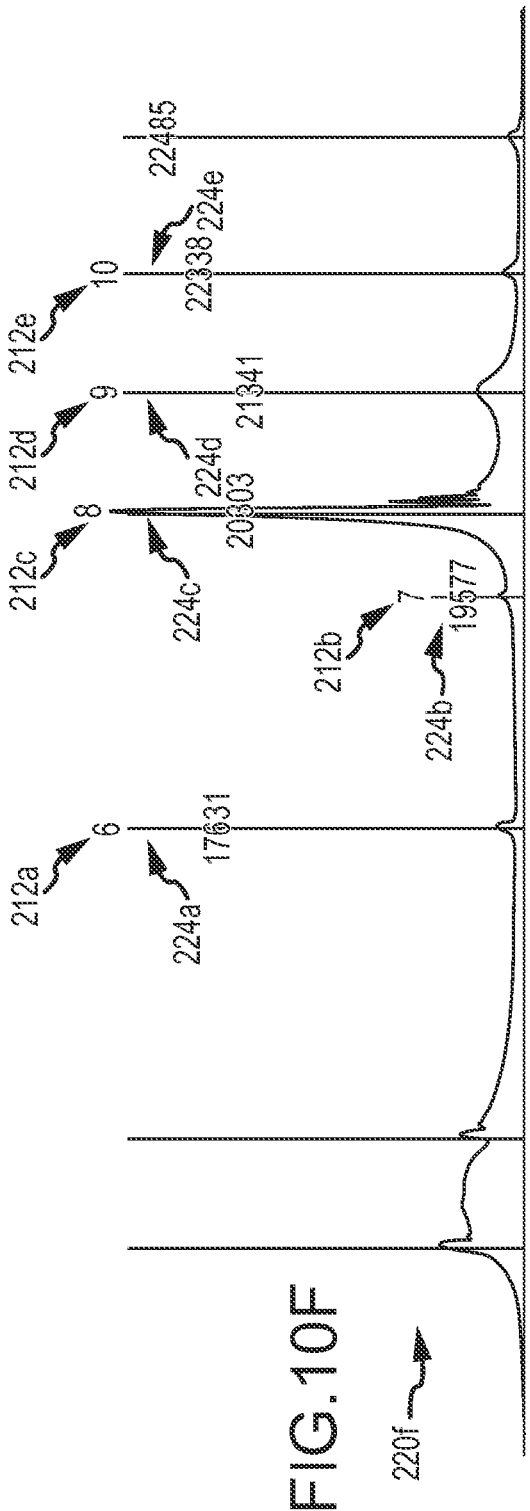
Figure 10G:
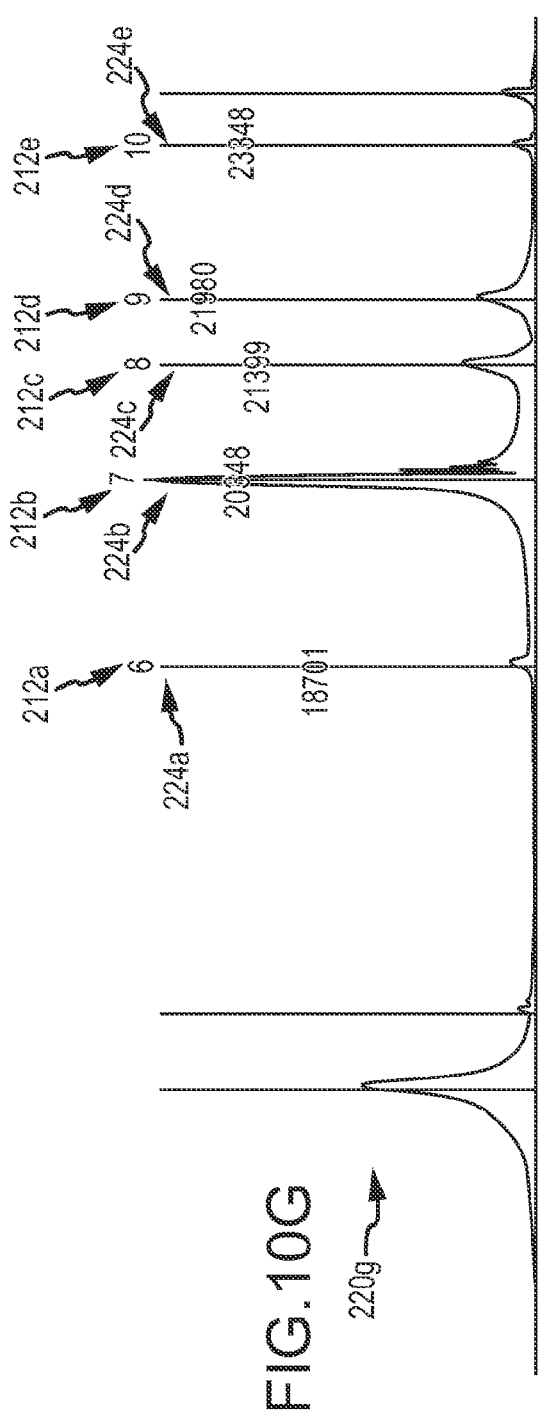
Figure 10H:
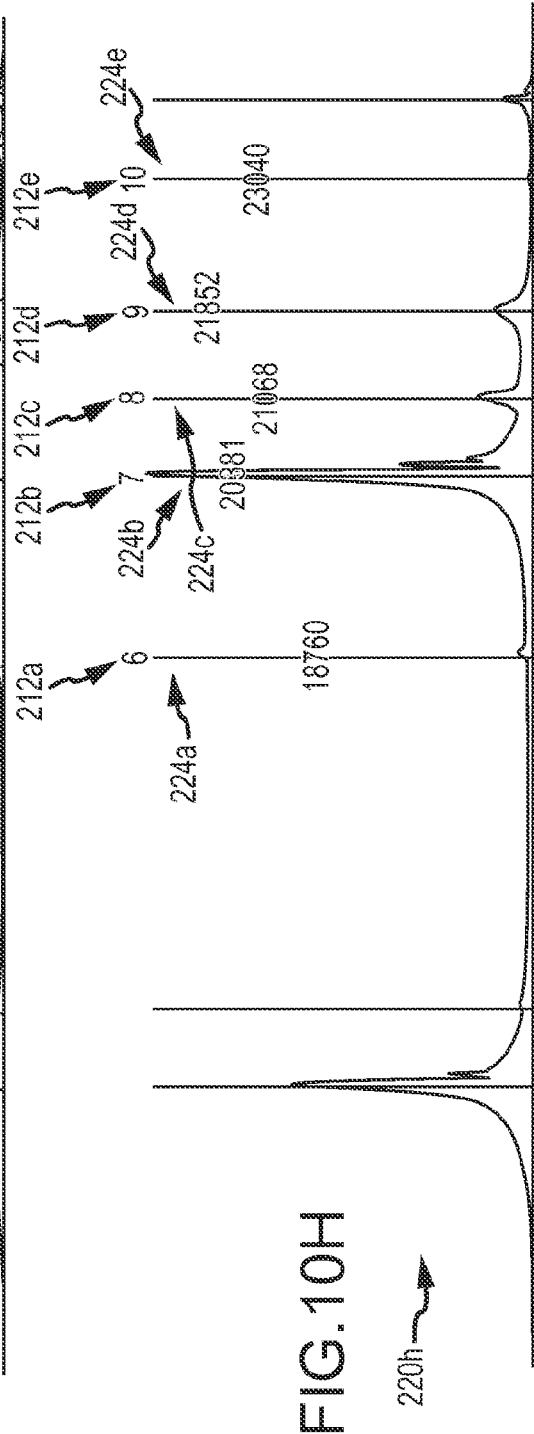

Many of the resonance frequency peaks in one resonance data spectra will "line up" with the resonance frequency peaks on another resonance data spectra. Such may not always be the case. For instance, compare the resonance frequency peaks of FIG. 10E with the resonance frequency peaks of FIG. 10F. Without consulting the surface vibration data of FIGS. 9A-J, it is possible that resonance frequency peak 224c in FIG. 10F could be associated with vibrational mode 212b (note how resonance frequency peak 224b in FIG. 10E lines up with resonance frequency peak 224c in FIG. 10F). However, using surface vibration data in the assessment of resonance data, frequency peak 224c in FIG. 10F is associated with vibrational mode 212c (versus vibrational mode 212b). In this regard and illustrating how reviewing the surface vibration data assists in assigning frequency peaks in resonance data to the correct vibration mode: 1) for the drive frequency 210f in FIG. 9F, the mode frequency 214a (17,610 Hz) associated with the vibrational mode 212a (mode 6) of the surface vibration data of FIG. 9F may be used to identify the corresponding resonance frequency peak 224a (17,631 Hz) in the resonance data 220f of FIG. 10F that should be associated with the vibrational mode 212a (mode 6); 2) for the drive frequency 210f in FIG. 9F, the mode frequency 214b (19,541 Hz) associated with the vibrational mode 212b (mode 7) of the surface vibration data of FIG. 9F may be used to identify the corresponding resonance frequency peak 224b (19,577 Hz) in the resonance data 220f of FIG. 10F that should be associated with the vibrational mode 212b (mode 7); 3) for the drive frequency 210f in FIG. 9F, the mode frequency 214c (20,243 Hz) associated with the vibrational mode 212c (mode 8) of the surface vibration data of FIG. 9F may be used to identify the corresponding resonance frequency peak 224c (21,303 Hz) in the resonance data 220f of FIG. 10F that should be associated with the vibrational mode 212c (mode 8); 4) for the drive frequency 210f in FIG. 9F, the mode frequency 214d (21,244 Hz) associated with the vibrational mode 212d (mode 9) of the surface vibration data of FIG. 9F may be used to identify the corresponding resonance frequency peak 224d (21,341 Hz) in the resonance data 220f of FIG. 10F that should be associated with the vibrational mode 212*d* (mode 9); and 5) for the drive frequency 210*f* in FIG. 9F, the mode frequency 214*e* (22,290 Hz) associated with the vibrational mode 212*e* (mode 10) of the surface vibration data of FIG. 9F may be used to identify the corresponding resonance frequency peak 224*e* (22,338 Hz) in the resonance data 220*f* of FIG. 10F that should be associated with the vibrational mode 212*e* (mode 10).

Figure 11:
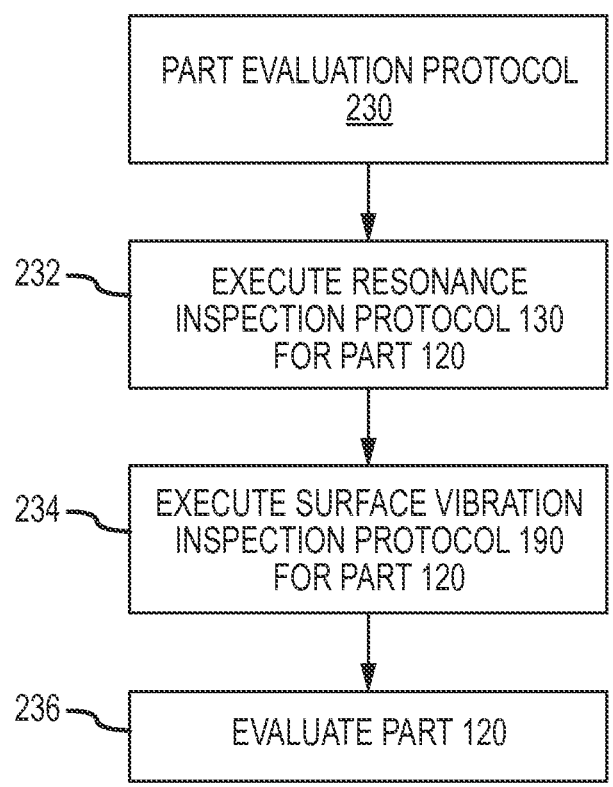
FIG. 11 is one embodiment of a part evaluation protocol for a part-under-test, which utilizes both a resonance inspection and a surface vibration inspection.

FIG. 11 presents one embodiment of a part evaluation protocol 230 that may be implemented using the resonance inspection tool 100 (FIG. 3) and the surface vibration inspection tool 100' (FIG. 8A) in accordance with the foregoing. The part evaluation protocol 230 may be utilized to assess a part 120 of any appropriate type, including without limitation new production parts, in-service parts, and non-OEM parts. A part 120 may be evaluated pursuant to the protocol 230 to determine if it complies with an OEM part (or any other appropriate control group defined by one or more parts or part specifications).

The resonance inspection protocol 130 (FIG. 5) may be executed for the part 120 (step 232) in the part evaluation protocol 230 of FIG. 11. The surface vibration inspection protocol 190 (FIG. 8B) may be executed for the part 120 (step 234). Steps 232 and 234 may be executed at any appropriate time, including sequentially (in any order), simultaneously, or in partially overlapping relation. The data gathering steps for the resonance inspection protocol 130 (step 134) and for the surface vibration inspection protocol 190 (step 194) may be simultaneously executed—both resonance data and surface vibration data may be acquired for a given drive frequency being used to excite the part 120 (step 132 of the resonance inspection protocol 130; step 192 of the surface vibration inspection protocol 190). In any case, the part 120 is evaluated pursuant to step 236 of the part evaluation protocol 230 (e.g., utilizing the results of the resonance inspection protocol 130 and/or the surface vibration inspection protocol 190). The resonance inspection protocol 130 and the surface vibration inspection protocol 190 may be utilized in a variety of manners for purposes of step 236 of the part evaluation protocol 230.

Figure 12:
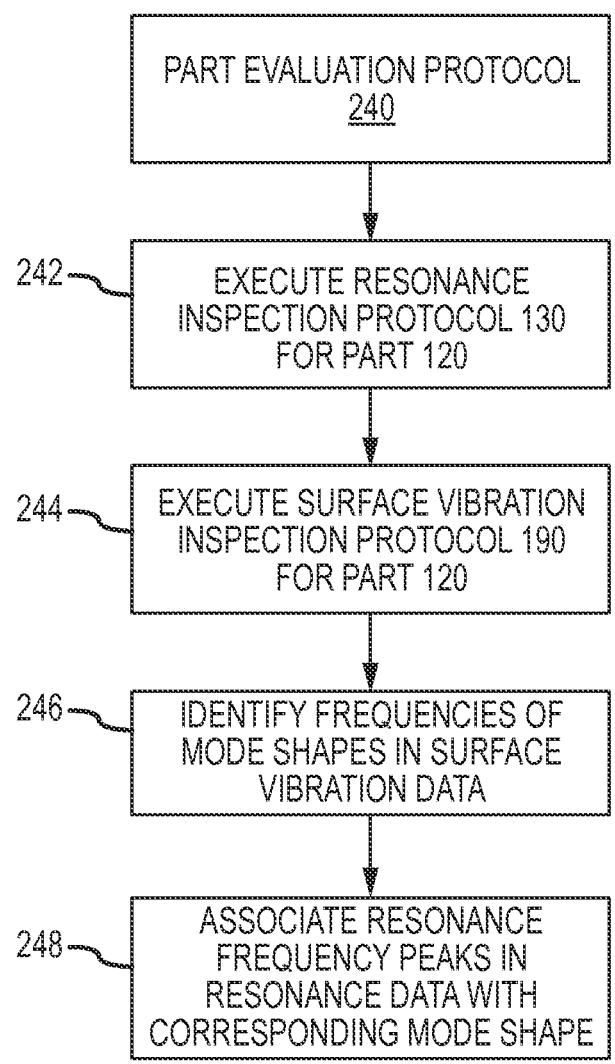
FIG. 12 is one embodiment of a part evaluation protocol for a part-under-test, which utilizes both a resonance inspection and a surface vibration inspection, and where mode shapes in the surface vibration data are used to identify resonance frequency peaks in the resonance data.

The surface vibration data (surface vibration inspection protocol 190—FIG. 8B) may be used to enhance the assessment of the resonance data (resonance inspection protocol 130—FIG. 5). A representative embodiment of this type of a part evaluation protocol is illustrated in FIG. 12, is identified by reference numeral 240, and may be implemented using the resonance inspection tool 100 (FIG. 3) and the surface vibration inspection tool 100' (FIG. 8A) in accordance with the foregoing. The resonance inspection protocol 130 (FIG. 5) may be executed for the part 120 (step 242). The surface vibration inspection protocol 190 (FIG. 8B) may be executed for the part 120 (step 244). Steps 242 and 244 may be executed in accordance with the discussion of the part evaluation protocol 230 of FIG. 11.

The frequencies of at least certain vibrational modes or mode shapes in the surface vibration data (acquired from the execution of the surface vibration inspection protocol 190—step 244) may be identified pursuant to step 246 of the part evaluation protocol 240. One or more resonance frequency peaks in the resonance data (acquired from the execution of the resonance inspection protocol 130—step 242) may be associated with the corresponding vibrational mode or mode shape pursuant to step 248. Generally and as discussed above in relation to FIGS. 9A-J and FIGS. 10A-J, the surface vibration data may be used to increase the potential that the resonance frequency peaks in the resonance data, that are used in the assessment of a part 120, are assigned to the proper vibrational mode or mode shape for comparison with at least one resonance standard (step 154 of the in-service part sort protocol 150 of FIG. 6; step 174 of the new production part sort protocol 170 of FIG. 7).

Figure 13:
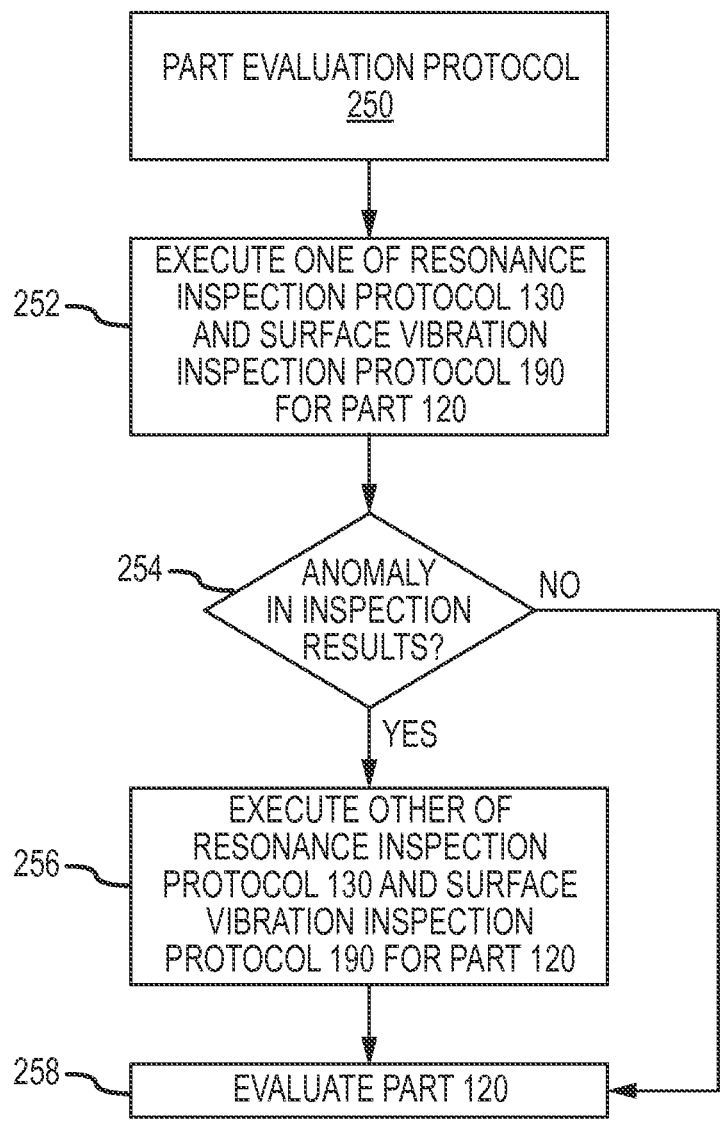
FIG. 13 is one embodiment of a part evaluation protocol for a part-under-test, where anomaly identification determines whether one or both of a resonance inspection and a surface vibration inspection are conducted.

An anomaly-based part evaluation protocol is illustrated in FIG. 13, is identified by reference numeral 250, and may be implemented using the resonance inspection tool 100 (FIG. 3) and the surface vibration inspection tool 100' (FIG. 8A) in accordance with the foregoing. Either the resonance inspection protocol 130 (FIG. 5) or the surface vibration inspection protocol 190 (FIG. 8B) may be executed for the part 120 (step 252). Depending upon the inspection protocol that is executed pursuant to step 252, either the frequency response of the part 120 is assessed (step 136 of the resonance inspection protocol 130 of FIG. 5 may be conducted for step 252 of the part evaluation protocol 250 of FIG. 13) or the surface vibration response of the part 120 is assessed (step 198 of the surface vibration inspection protocol 190 of FIG. 8B may be conducted for step 252 of the part evaluation protocol 250 of FIG. 13) pursuant to step 254 of the part evaluation protocol 250 of FIG. 13. If at least one anomaly is identified (step 254) by the executed inspection (step 252), the other of the resonance inspection protocol 130 and the surface vibration inspection protocol 190 is executed pursuant to step 256. In any case, the part evaluation protocol 250 proceeds to step 258 for an evaluation of the part 120. As such, the part evaluation protocol 250 is configured to execute only the resonance inspection protocol 130 or the surface vibration inspection protocol 194 for the part 120, unless the executed inspection identifies at least one anomaly, in which case both inspections would be conducted on the part 120 to facilitate its evaluation (step 258).

Figure 14:
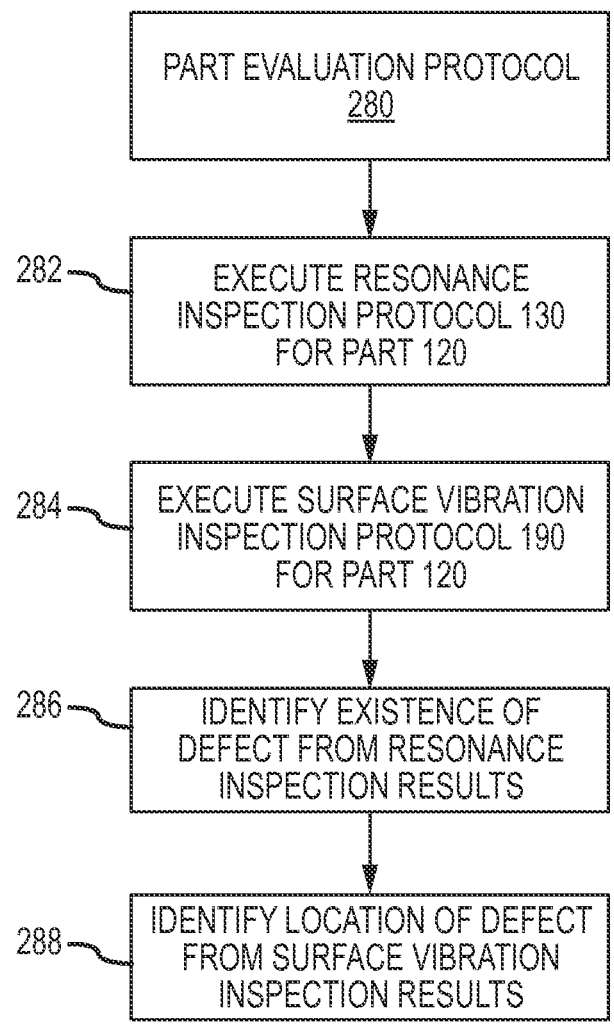
FIG. 14 is one embodiment of a part evaluation protocol for a part-under-test, where a resonance inspection is used to identify an existence of a defect, and where a surface vibration inspection is used to identify a location of an identified defect.

What may be characterized as another anomaly-based part evaluation protocol is illustrated in FIG. 14, is identified by reference numeral 280, and may be implemented using the resonance inspection tool 100 (FIG. 3) and the surface vibration inspection tool 100' (FIG. 8A) in accordance with the foregoing. The resonance inspection protocol 130 (FIG. 5) may be executed for the part 120 (step 282). The surface vibration inspection protocol 190 (FIG. 8B) may be executed for the part 120 (step 284). Steps 282 and 284 may be executed in accordance with the discussion of the part evaluation protocol 230 of FIG. 11. In the case of the part evaluation protocol 280, the resonance data from the execution of the resonance inspection protocol 130 is used to identify the existence of one or more defects in the part (step 286), while the surface vibration data from the execution of the surface vibration inspection protocol 190 is used to identify the location of the identified defect(s) (step 288).

Steps 286 and 288 of the part evaluation protocol 280 of FIG. 14 may be phase shift-based. If the assessment of the frequency response of the part 120 (step 136 of the resonance inspection protocol 130 of FIG. 5) identifies a phase shift (e.g., in relation to the drive frequency—step 132 of the resonance inspection protocol 130), step 286 of the part evaluation protocol 280 of FIG. 14 may be configured to equate such a phase shift with the existence of a defect in the part 120. The surface vibration data from the surface vibration inspection protocol 190 of FIG. 8B may then be assessed (pursuant to its step 198) to attempt to identify a corresponding phase shift. If such a phase shift is identified in the surface vibration data, step 288 of the part evaluation protocol 280 may use this phase shift information to identify the location on the part 120 where this phase shift is occurring, and may be configured to equate this with the location of a defect in the part 120.

Steps 286 and 288 of the part evaluation protocol 280 of FIG. 14 may be amplitude shift-based. If the assessment of the frequency response of the part 120 (step 136 of the resonance inspection protocol 130 of FIG. 5) identifies an amplitude shift (e.g., in relation to the drive frequency—step 132 of the resonance inspection protocol 130), step 286 of the part evaluation protocol 280 of FIG. 14 may be configured to equate such an amplitude shift with the existence of a defect in the part 120. The surface vibration data from the surface vibration inspection protocol 190 of FIG. 8B may then be assessed (pursuant to its step 198) to attempt to identify a corresponding amplitude shift. If such an amplitude shift is identified in the surface vibration data, step 288 of the part evaluation protocol 280 may use this amplitude shift information to identify the location on the part 120 where this amplitude shift is occurring, and may be configured to equate this with the location of a defect in the part 120.

Modeling may be used in relation to the execution of steps 286 and 288 of the part evaluation protocol 280 of FIG. 14. One or more defects may be modeled in any appropriate manner in relation to the part 120. The resonance data acquired from the execution of the resonance inspection protocol 130 of FIG. 5 may be compared to the modeled defects (pursuant to its step 136) for purposes of identifying defects for step 286 of the part evaluation protocol 280 of FIG. 14. Similarly, the surface vibration data acquired from the execution of the surface vibration inspection protocol 190 of FIG. 8B may be compared to the modeled defects (pursuant to its step 198) for purposes of identifying the location of defects for step 288 of the part evaluation protocol 280 of FIG. 14.

Figure 15:
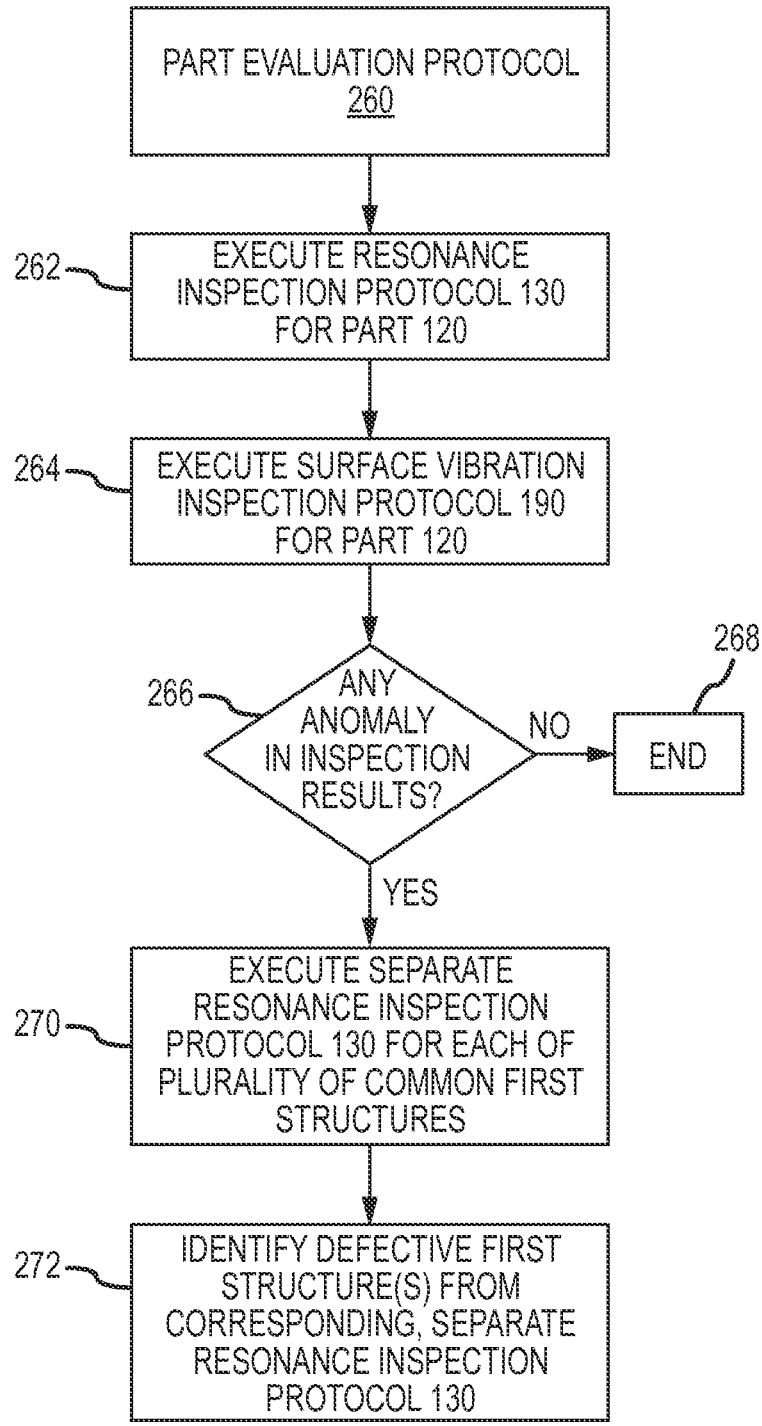
FIG. 15 is one embodiment of a part evaluation protocol for a part-under-test, where a separate resonance inspection is conducted on each of a plurality of first structures of a part-under-test in response to an anomaly being identified by a resonance and/or surface vibration inspection.

Yet another anomaly-based evaluation protocol is illustrated in FIG. 15, is, identified by reference numeral 260, is adapted for the case where the part 120 includes a plurality of common first structures (e.g., a plurality of similarly configured/sized fins; a plurality of similarly configured/sized blades mounted on a common body), and may be implemented using the resonance inspection tool 100 (FIG. 3) and the surface vibration inspection tool 100' (FIG. 8A) in accordance with the foregoing. The resonance inspection protocol 130 (FIG. 5) may be executed for the part 120 (step 262). The surface vibration inspection protocol 190 (FIG. 8B) may be executed for the part 120 (step 264). Steps 262 and 264 may be executed in accordance with the discussion of the part evaluation protocol 230 of FIG. 11. If the inspection results do not identify any anomalies, the protocol 260 terminates by execution of step 268. Otherwise (i.e., if at least one anomaly is identified pursuant to step 266), a separate resonance inspection protocol 130 is executed in relation to each of the first structures (step 270). The resonance inspections conducted on each of the first structures may be used to identify which of the first structures is defective (step 272).

A surface vibration inspection of the part 120 may be conducted for any purpose in relation to the part evaluation protocol 260 of FIG. 15. However, step 264 of the part evaluation protocol 260 may not be required in all instances. That is, if the frequency response of the part 120 alone is determined to be anomalous in any respect (e.g., step 136 of the resonance inspection protocol 130 of FIG. 5), the part evaluation protocol 260 of FIG. 15 may be configured to execute steps 270 and 272.

Figure 16:
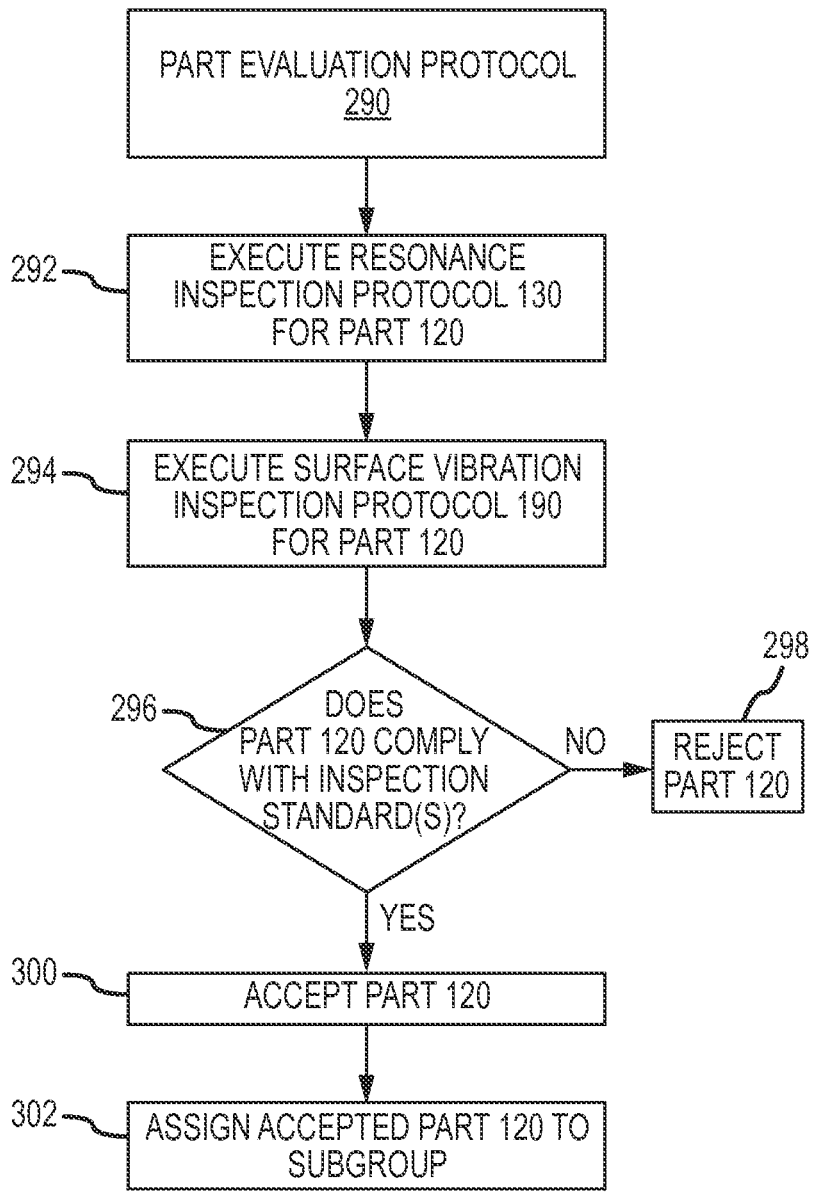
FIG. 16 is one embodiment of a part evaluation protocol for a part-under-test, where an accepted part may be assigned to a particular subgroup.

An evaluation protocol that relates to subgroups is illustrated in FIG. 16, is identified by reference numeral 290, and may be implemented using the resonance inspection tool 100 (FIG. 3) and the surface vibration inspection tool 100' (FIG. 8A) in accordance with the foregoing. The resonance inspection protocol 290 (FIG. 5) may be executed for the part 120 (step 292). The surface vibration inspection protocol 190 (FIG. 8B) may be executed for the part 120 (step 294). Steps 292 and 294 may be executed in accordance with the discussion of the part evaluation protocol 230 of FIG. 11. Step 296 is directed to determining whether the part 120 complies with it at least one inspection standard (e.g., a resonance standard for the resonance inspection protocol 130; a surface vibration standard for the surface vibration inspection protocol 190). Step 296 may be configured in accordance with steps 246 and 248 of the part evaluation protocol 240 of FIG. 12 (e.g., so that the surface vibration inspection protocol 190 is undertaken for the primary purpose of associating resonance frequency peaks in the resonance data (from execution of the resonance inspection protocol 130) with a corresponding vibrational mode or mode shape, which may then be compared with one or more resonance standards). In any case, if the part 120 does not comply with the inspection standard(s) associated with step 296, the protocol 290 proceeds to step 298 where the part 120 may be rejected. Otherwise, the protocol 290 proceeds to step 300 where the part 120 may be accepted. Moreover, the accepted part 120 may be assigned to one of a plurality of subgroups pursuant to step 302.

Accepted parts (step 300 of the part evaluation protocol 290) may be characterized as being a member of one of any appropriate number of subgroups for purposes of step 302 of the part evaluation protocol 290 of FIG. 16. The subgroups may be defined in any appropriate manner. For instance, membership of a part 122 in a given subgroup may be based upon resonant frequency alone (frequencies are bi-modal), surface vibration characteristics alone (surface vibration points to multiple groups), a combination of the two (resonant frequency in one subgroup, surface vibration characteristics in another subgroup). Subgroups may also be defined by other inputs (part variance, part mass or density, part age/condition (e.g., repaired or not)). Subgroups may have different sorting criteria applied—passed or failed by different standards. Subgroups may be established based upon part age (e.g., one subgroup may be for parts having "a lot of life left," while another subgroup may be for parts having only "a little life left"). Subgroups may be based upon a recommended part disposition (e.g., one subgroup may be parts that are recommended for use, one subgroup may be parts that are recommended for repair, one subgroup may be parts that are recommended to be scrapped).

Figure 17:
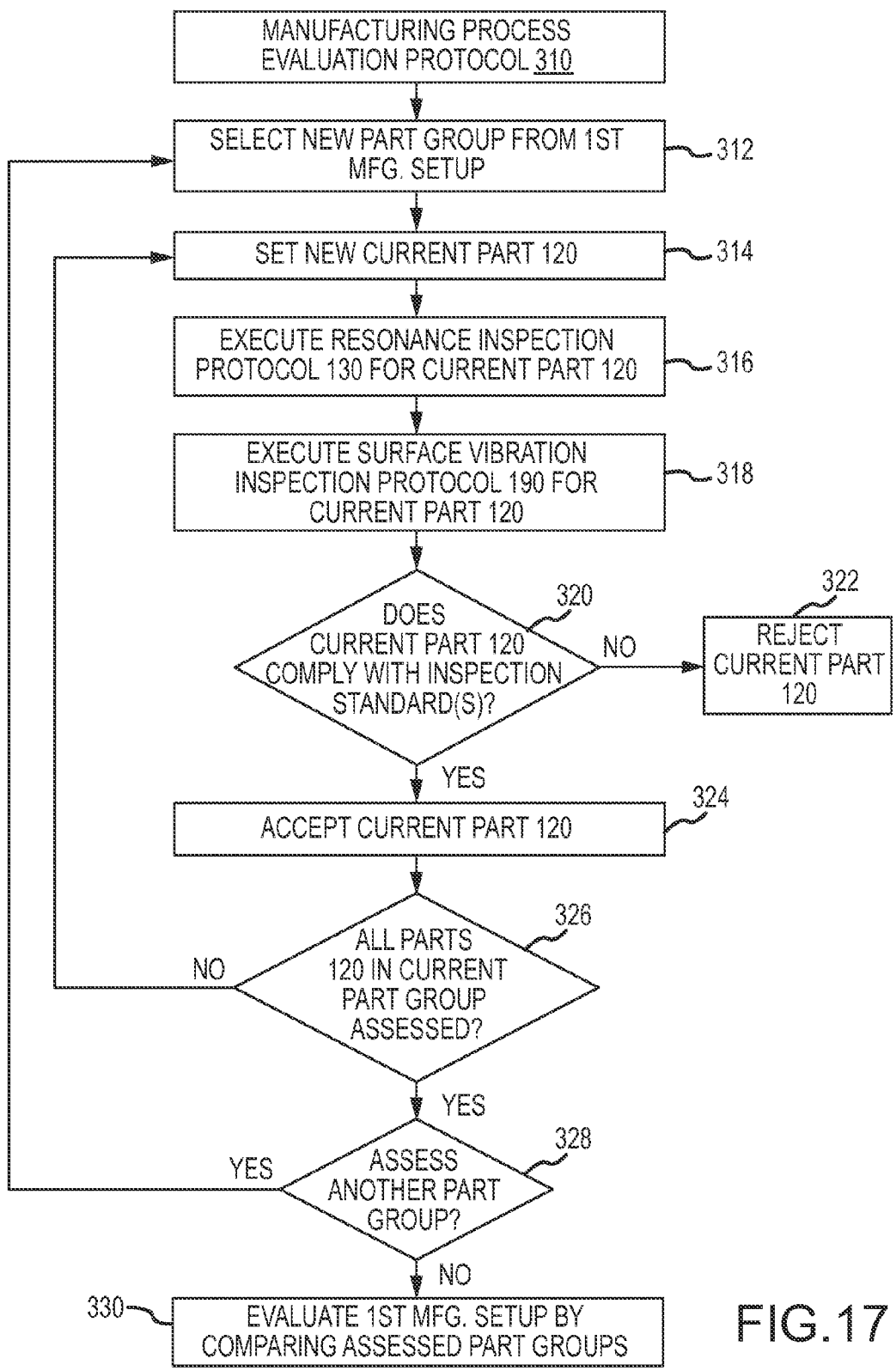
FIG. 17 is one embodiment of a manufacturing process evaluation protocol.

One embodiment of the manufacturing process evaluation protocol is illustrated in FIG. 17, is identified by reference numeral 310, and may be implemented using the resonance inspection tool 100 (FIG. 3) and the surface vibration inspection tool 100' (FIG. 8A) in accordance with the foregoing. Generally, the manufacturing process evaluation protocol 310 may be used to assess a first manufacturing setup by comparing parts 120 made by the first manufacturing setup over a first time frame (for instance on shift 1 of day 1 of month 1), with parts made by the same first manufacturing setup over a second time frame (for instance on shift 1 of on day 1 of month 2).

Step 312 of the protocol 310 of FIG. 17 is directed to selecting a new part group (e.g., a collection of parts 120 produced from first manufacturing setup over a given time frame). Each part 120 in the part group from step 312 may be assessed in accordance with the following. Step 314 is directed to selecting or setting a new current part 120 from the part group (step 312) for evaluation purposes. A resonance inspection protocol 130 (FIG. 5) may be executed for the current part 120 (step 316). A surface vibration inspection protocol 190 (FIG. 8B) may be executed for the current part 120 (step 318). Steps 316 and 318 may be executed in accordance with the discussion of the part evaluation protocol 230 of FIG. 11.

Step 320 of the protocol 310 of FIG. 17 is directed to determining whether the current part 120 complies with it at least one inspection standard (e.g., a resonance standard for the resonance inspection protocol 130; a surface vibration standard for the surface vibration inspection protocol 190). Step 320 may be configured in accordance with steps 246 and 248 of the part evaluation protocol 240 of FIG. 12 (e.g., so that the surface vibration inspection protocol 190 is undertaken for the primary purpose of associating resonance frequency peaks in the resonance data (from execution of the resonance inspection protocol 130) with a corresponding vibrational mode or mode shape, which may then be compared with at least one resonance standard). In any case, if the current part 120 does not comply with the inspection standard(s) associated with step 320, the protocol 310 proceeds to step 322 where the current part 120 may be rejected. Otherwise, the protocol 310 proceeds to step 324 where the current part 120 may be rejected.

If not all parts 120 in the current part group have been assessed in accordance with the foregoing, the protocol 310 proceeds from step 326 back to step 314 for repetition in accordance with the foregoing. Otherwise, the protocol 310 proceeds to step 328, and which is directed to determining if another part group is to be assessed. If so, the protocol proceeds from step 328 back to step 312 for repetition in accordance with the foregoing.

As noted above, a second part group (another collection of parts 120 made by the same first manufacturing setup) may be defined at a later point in time in relation to the first part group. In any case, once data has been acquired on two or more part groups, the protocol 310 proceeds to step 330 where the first manufacturing setup may be evaluated by comparing the part groups assessed in accordance with the foregoing. Manufacturing operations may be assessed by the "mean" and the "spread" of the resonance data they produce. The mean and spread could be for "all resonance mode" measurements, or only a selection, based on relevance to the particular operation/targeted condition. The evaluation of step 330 may entail evaluating cumulative statistics for a variety of resonances, or information for single resonances. Where multiple resonances are evaluated, the evaluation of step 330 may be an evaluation of the "variation" among these in the "reference standard" relative to the population under evaluation (from the manufacturing operation). "More variation" may indicate a change in the pattern of the multiple resonances that indicates a difference (e.g., due to manufacturing operations). Manufacturing operations could also be evaluated for purposes of step 330 by the change "before and after" the operation, if data has been collected before. The standard would show how much the operation is "supposed to" change the part, and the "after" measurements could be compared to this standard.

Figure 18:
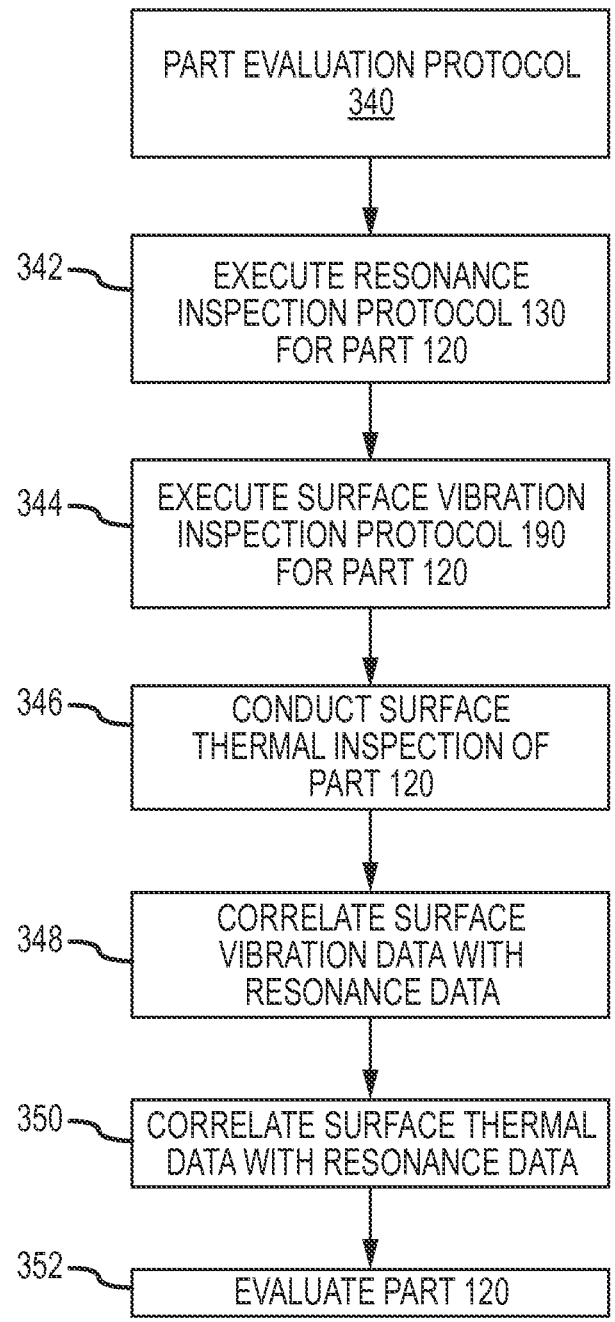
FIG. 18 is one embodiment of a part evaluation protocol for a part-under-test, where resonance data from a resonance inspection may be correlated with surface vibration data and/or surface thermal data.

Another embodiment of a part evaluation protocol is illustrated in FIG. 18 and is identified by reference numeral 340. A resonance inspection protocol 130 (FIG. 5) may be executed for the part 120 (step 342). A surface vibration inspection protocol 190 (FIG. 8B) may be executed for the part 120 (step 344). Steps 342 and 344 may be executed in accordance with the discussion of the part evaluation protocol 230 of FIG. 11. A surface thermal inspection may also be conducted of the part 120 pursuant to step 346. The surface vibration data (from execution of the surface vibration protocol 190—step 344) is correlated with the resonance data (from execution of the resonance inspection protocol 130—step 342) pursuant to step 348. Similarly, the thermal inspection data (from execution of step 346) is correlated with the resonance data (from execution of the resonance inspection protocol 130—step 342) pursuant to step 350. The part 120 may then be evaluated pursuant to step 352. If the frequency analysis (described above) points to variation due to the manufacturing operation, the surface vibration analysis could be consulted for "explanation." If the surface vibration data is not anomalous, this points to a different source than if the surface vibration is also anomalous.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such, or other embodiments and with various modifications required by the particular application(s) or use(s) of the present invention. It is intended that the appended claims be construed to include alternative embodiments to the extent permitted by the prior art.

What is claimed is:

1. A method of evaluating a part, wherein a resonance inspection comprises exciting a part-under-test at a plurality of input frequencies and obtaining a frequency response of a part-under-test at each of said plurality of input frequencies, wherein a surface vibration inspection comprises vibrating a part-under-test and assessing surface vibrations of a part-under test, and wherein said method comprises the steps of:
conducting a first inspection of a first part-under-test, wherein said first inspection comprises performing said resonance inspection on said first part-under-test;
conducting a second inspection of said first part-under-test, wherein said second inspection comprises performing said surface vibration inspection on said first part-under-test; and
evaluating said first part-under-test based upon each of said first and second inspections, wherein said first part-under-test comprises a plurality of common first structures, wherein said evaluating step further comprises:
identifying an anomaly in results from at least one of said first and second inspections of said first part-under-test; and
conducting a separate said resonance inspection on each first structure of said plurality of common first structures for said first part-under-test, all in response to and after said identifying step, wherein each said resonance inspection of each said first structure from said conducting step of said evaluating step is in addition to the previous-in-time said resonance inspection of said first part-under-test from said conducting a first inspection step.

2. The method of claim 1, wherein said resonance inspection comprises using a first transducer that excites said first part-under-test at each of multiple frequencies, and also using said first transducer to measure said frequency response of said first part-under-test.

3. The method of claim 1, wherein said resonance inspection comprises obtaining said frequency response of said first part-under-test using at least one receive transducer that is maintained in spaced relation to said first part-under-test throughout said resonance inspection.

4. The method of claim 3, wherein said at least one receive transducer comprises a laser.

5. The method of claim 1, wherein said resonance inspection comprises obtaining said frequency response of said first part-under-test using laser vibrometry.

6. The method of claim 5, wherein said frequency response is obtained from a single location on said first part-under-test using laser vibrometry.

7. The method of claim 5, wherein said frequency response is obtained by laser scanning multiple locations on said first part-under-test.

8. The method of claim 1, wherein said resonance inspection comprises exciting said first part-under-test using at least one drive transducer that is maintained in spaced relation to said first part-under-test throughout said resonance inspection.

9. The method of claim 8, wherein said at least one drive transducer comprises a laser.

10. The method of claim 1, wherein said surface vibration inspection is selected from the group consisting of holographic interferometry, laser vibrometry, laser Doppler velocimetry, scanning laser vibrometry, and 2-d and 3-d scanning laser vibrometry.

11. The method of claim 1, wherein said evaluating step comprises determining if said first part-under-test is equivalent to a control group.

12. The method of claim 1, further comprising the step of disposing said first part-under-test in a fixture, wherein each of said first and second inspections are completed with said first part-under-test remaining in said fixture.

13. The method of claim 1, wherein said evaluating step comprises using results from said first inspection to assess an anomaly in results from said second inspection.

14. The method of claim 1, wherein said evaluating step comprises using results from said second inspection to assess an anomaly in results from said first inspection.

15. The method of claim 1, wherein said evaluating step comprises using results from said second inspection to associate a first resonance frequency peak in resonance inspection results with a vibrational mode.

16. The method of claim 15, wherein each said vibrational mode is selected from the group consisting of any one of multiple orders of each of a bending mode, a torsional mode, longitudinal modes, coupling modes, flexural modes, and axial modes.

17. The method of claim 1, wherein said evaluating step comprises using results from said second inspection to associate each of a plurality of resonance frequency peaks in resonance inspection results with a different vibrational mode.

18. The method of any of claim 1, wherein said evaluating step comprises using results from said second inspection to identify at least one vibrational mode in results from said first inspection.

19. The method of claim 1, wherein said second inspection comprises identifying a plurality of mode shapes in results from said second inspection for use by said first inspection.

20. The method of claim 19, wherein said identifying a plurality of mode shapes comprises associating a frequency with each of said plurality of mode shapes, and wherein said first inspection comprises utilizing said frequencies associated with said plurality of mode shapes.

21. The method of claim 1, wherein said evaluating step further comprises comparing results from said first inspection with at least one resonance standard, wherein each said resonance standard is stored on a computer-readable storage medium, wherein said evaluating step comprises using at least one processor, and wherein each said resonance standard is based upon spectra from conducting a separate said resonance inspection on each of a plurality of parts.

22. The method of claim 21, wherein said resonance standard is further based upon conducting a separate said surface vibration inspection on each of said plurality of parts, and correlating results from said surface vibration inspection with results from said resonance inspection for each of said plurality of parts.

23. The method of claim 22, wherein said resonance standard comprises a plurality of subgroups, wherein said method further comprises defining said subgroups using results from said surface vibration analysis on each of said plurality of parts and from said resonance inspection for each of said plurality of parts.

24. The method of claim 21, wherein said resonance standard is further based upon conducting a separate thermal surface analysis on each of said plurality of parts during said resonance inspection of said plurality of parts, and correlating results from said thermal surface analysis with results from said resonance inspection for each of said plurality of parts.

25. The method of claim 1, wherein said evaluating step further comprises comparing results from said first inspection with at least one resonance standard, wherein said evaluating step further comprises using results from said second inspection to compare said results from said first inspection with said at least one resonance standard.

26. The method of claim 1, wherein said evaluating step comprises identifying a phase shift using said first inspection, and thereafter using said second inspection to identify a cause of said phase shift.

27. The method of claim 1, wherein said evaluating step comprises identifying an existence of a defect comprising identifying a phase shift in results from said first inspection, and wherein said evaluating step further comprises identifying a location of said defect comprising identifying a phase shift in results from said second inspection.

28. The method of claim 1, wherein said evaluating step comprises identifying a change in amplitude of at least one resonance frequency peak using said) first inspection, and thereafter using said second inspection to identify a cause of said phase shift.

29. The method of claim 1, wherein said evaluating step comprises identifying an existence of a defect comprising identifying an amplitude shift in results of said first inspection, and wherein said evaluating step further comprises identifying a location of said defect comprising identifying an amplitude shift in results from said second inspection.

30. The method of claim 1, further comprising the step of modeling a first defect, wherein said evaluating step comprises at least one of comparing results from said first inspection with results from said modeling step and comparing results from said second inspection with results from said modeling step.

* * * * *